United States Patent
Deisher et al.

(10) Patent No.: US 6,486,304 B1
(45) Date of Patent: Nov. 26, 2002

(54) ANTIBODIES AND METHODS OF MAKING ANTIBODIES TO HUMAN THYROID PROTEIN ZSIG45

(75) Inventors: Theresa A. Deisher, Seattle; Paul O. Sheppard, Redmond, both of WA (US)

(73) Assignee: Zymogenetics, Inc., Seattle, WA (US)

( * ) Notice: Subject to any disclaimer, the term of this patent is extended or adjusted under 35 U.S.C. 154(b) by 0 days.

(21) Appl. No.: 09/523,462

(22) Filed: Mar. 10, 2000

Related U.S. Application Data

(62) Division of application No. 09/320,623, filed on Dec. 1, 1998, now Pat. No. 6,140,084.
(60) Provisional application No. 60/067,263, filed on Dec. 3, 1997.

(51) Int. Cl.[7] .................... C07K 16/00; A61K 39/395; A61K 38/00
(52) U.S. Cl. ................ 530/389.1; 530/389.2; 530/388.15; 530/388.24; 424/134.1; 424/139.1; 424/145.1; 514/2; 514/12
(58) Field of Search ............... 530/389.1, 389.2, 530/388.15, 388.24; 424/134.1, 139.1, 145.1; 514/2, 12

(56) References Cited

PUBLICATIONS

Strausberg, EMBL Database, Accession No. g3754416, 1998.
EMBL Database, Accession No. Z99570, 1997.
Eggo et al., *Mol. Cell. Endocrinol.*, 100:97–102, 1994.
Life SEQ™ Clone Information Results, Incyte Pharmaceuticals, Inc., 1996.
Life SEQ™ Clone Information Results, Incyte Pharmaceuticals, Inc., 1997.
Life SEQ™ Library Information Results, Incyte Pharmaceuticals, Inc., 1996.
Life SEQ™ Library Information Results, Incyte Pharmaceuticals, Inc., 1997.

*Primary Examiner*—Yvonne Eyler
*Assistant Examiner*—Fozia Hamud
(74) *Attorney, Agent, or Firm*—Jennifer K. Johnson

(57) ABSTRACT

The present invention relates to polynucleotide and polypeptide molecules for zsig45, a novel human protein expressed in thyroid. The polypeptides, and polynucleotides encoding them, may be used for detecting human disease states and chromosomal abnormalities, and as a therapeutic. The present invention also includes antibodies to the zsig45 polypeptides.

6 Claims, No Drawings

US 6,486,304 B1

ANTIBODIES AND METHODS OF MAKING ANTIBODIES TO HUMAN THYROID PROTEIN ZSIG45

REFERENCE TO RELATED APPLICATIONS

The present application is a divisional application of U.S. patent application Ser. No. 09/320,623 filed Dec. 1, 1998 now U.S. Pat. No. 6,140,084, which claims benefit to Provisional application No. 60/067,263 filed on Dec. 3, 1997. Under 35 U.S.C. §119(e)(1), this application claims benefit of said Provisional Application.

BACKGROUND OF THE INVENTION

Proliferation and differentiation of cells of multicellular organisms are controlled by hormones and polypeptide growth factors. These diffusable molecules allow cells to communicate with each other and act in concert to regulate cell proliferation and organ development; and regulate repair and regeneration of damaged tissue. Hormones and growth factors influence cellular metabolism by binding to receptors. Receptors may be integral membrane proteins. that are linked to signaling pathways within the cell. Other classes of receptors are soluble molecules, such as transcription factors. Hormonal effects, including hormone and soluble receptor interaction, are essential for effective thyroid function.

The thyroid gland is a major endocrine gland during normal human growth and development. In adults, the major role of the thyroid is to maintain metabolic stability, primarily through thyroid hormone production and regulation. Virtually every organ in the body is affected by thyroid hormones. Thus, thyroid malfunction is associated with several disease states. Thyroid diseases are relatively common, occurring in the form of thyroid gland size and shape abnormalities (goiter) and abnormalities in thyroid hormone secretion. Thyroid malfunction may also result from non-thyroidal illnesses or nutrient deficiencies that alter thyroid physiology. Examples of common thyroid diseases are thyrotoxicosis, hypothyroidism, Grave's disease, hyperthyroidism and thyroid tumors. For general review see, Felig, P, Baxter, J. D. and Frohman, L. A. (eds.), *Endocrinology and Metabolism*, McGraw Hill, NY, 3rd ed., 1995, pp. 432–553; and Bennett, J. C. and Plum, F. (eds.), *Textbook of Medicine*, W.B. Saunders Co., Philadelphia, 20th ed., 1996, pp. 1227–1245.

The most extensively studied thyroid hormones are thyroxine (T4), triiodothyronine (T3) and thyroid stimulating hormone (TSH). T4 is produced exclusively in the thyroid, whereas T3 is produced both by the thyroid and by extra-thyroidal enzymatic 5'-deiodination of T4. Both T3 and T4 are secreted and are derived from enzymatic cleavage of thyroglobulin; thyroglobulin, a major thyroid protein, is the intracellular storage form of T4 and T3. Both the biosynthesis and secretion of T4 and T3 are stimulated by pituitary TSH; which, in turn, is inhibited by circulating T3 and T4 and stimulated by hypothalamic thyrotropin-releasing hormone (TRH).

T3 functions as a ligand for thyroid hormone nuclear receptors, which mediate all known physiologic actions of thyroid hormone. These receptors are members of the steroid nuclear receptor superfamily; they bind DNA and activate mRNA transcription. The thyroid receptor has different activities when bound or not bound by its acidic T3 ligand. In circulation, T4 and T3 are bound by several different serum proteins until they reach their sites of action in various organs and tissues.

Thyroid hormones modulate a wide number of metabolic processes by regulating the production and activity of various enzymes, the production and metabolism of other hormones, and utilization of substrates, vitamins, and minerals. Not all of these effects are due to T3 transcriptional regulation. For example, non-nuclear actions include amino acid and sugar transport stimulation in lymphoid cells, calcium-ATPase activity in red blood cells and heart cells, and other membrane interactions. For review of the metabolic effect and diseases of thyroid hormones, see Braverman, L. E. (ed.), *Diseases of the Thyroid*, Humana Press, Totowa, N.J., 1997. Other known effectors contribute to this complex physiologic scheme. Currently unknown effectors are probably important as well.

There remains a need in the art to further elucidate thyroid-related physiology and to provide additional regulatory molecules. Of particular interest are regulatory proteins, including additional thyroid hormones, that influence thyroid function or are secreted from thyroid with extrathymic effects. Such hormones would be useful for, inter alia, restoring normal thyroid function in patients suffering various thyroid ailments and as targets for the development of small-molecule drugs. The demonstrated in vivo activities of known thyroid hormones illustrates the enormous clinical potential of, and need for, other thyroid hormones, their agonists and antagonists. The present invention provides such polypeptides for these and other uses that should be apparent to those skilled in the art from the teachings herein.

SUMMARY OF THE INVENTION

In one aspect, the present invention provides, an isolated polynucleotide that encodes a polypeptide comprising a sequence of amino acid residues that is at least 90% identical to an amino acid sequence selected from the group consisting of: (a) the amino acid sequence as shown in SEQ ID NO:2 from amino acid number 47 (Lys) to amino acid number 114 (Asp) of SEQ ID NO:2; (b) the amino acid sequence as shown in SEQ ID NO:4 from amino acid number 1 (Met) to amino acid number 85 (Asp); (c) the amino acid sequence as shown in SEQ ID NO:3 from amino acid number 1 (Met) to amino acid number 89 (Asp); (d) the amino acid sequence as shown in SEQ ID NO:2 from amino acid residue number 1 (Met) to amino acid residue number 114 (Asp). In one embodiment, the present invention provides an isolated polynucleotide molecule selected from the group consisting of: (a) polynucleotide molecules comprising a nucleotide sequence as shown in SEQ ID NO:1 from nucleotide 219 to nucleotide 422; (b) polynucleotide molecules comprising a nucleotide sequence as shown in SEQ ID NO:1 from nucleotide 168 to nucleotide 422; (c) polynucleotide molecules comprising a nucleotide sequence as shown in SEQ ID NO:1 from nucleotide 156 to nucleotide 422; (d) polynucleotide molecules comprising a nucleotide sequence as shown in SEQ ID NO:1 from nucleotide 82 to nucleotide 422; and (e) polynucleotide molecules complementary to (a), (b), (c), or (d). In another embodiment, the polynucleotide disclosed above comprises nucleotide 1 to nucleotide 342 of SEQ ID. NO:15. In another embodiment, the polynucleotide disclosed above consists of a sequence of amino acid residues that is at least 90% identical the amino acid sequence as shown in SEQ ID NO:2 from amino acid number 47 (Lys) to amino acid number 114 (Asp) of SEQ ID NO:2. In another embodiment, the polynucleotide disclosed above consists of a sequence of amino acid residues that is as shown in SEQ ID NO:2 from amino acid number 47 (Lys) to amino acid number 114 (Asp) of SEQ ID NO:2. In another embodiment, the polynucleotide disclosed above encodes a polypeptide, wherein the polypeptide contains motifs 1 through 5.

In a second aspect, the present invention provides an expression vector comprising the following operably linked elements: a transcription promoter; a DNA segment encoding a zsig45 polypeptide that is 90% identical to and amino acid sequence as shown in SEQ ID NO:2 from amino acid number 47 (Lys) to amino acid number 114 (Asp) of SEQ ID NO:2; and a transcription terminator. In one embodiment, the expression vector disclosed above further comprises a secretory signal sequence operably linked to the DNA segment. In another embodiment, the expression vector disclosed above comprises a secretory signal sequence selected from the group consisting of: (a) amino acids 1 through 46 of SEQ ID NO:2; (b) amino acids 1 through 21 of SEQ ID NO:3; and (c) amino acids 1 through 17 of SEQ ID NO:4.

In a third aspect, the present invention provides a cultured cell into which has been introduced an expression vector as disclosed above, wherein the cell expresses a polypeptide encoded by the DNA segment.

In a fourth aspect, the present invention provides a DNA construct encoding a fusion protein, the DNA construct comprising: a first DNA segment encoding a polypeptide that is at least 90% identical to a sequence of amino acids selected from the group consisting of: (a) amino acids 1 through 46 of SEQ ID NO:2; (b) amino acids 1 through 21 of SEQ ID NO:3; and (c) amino acids 1 through 17 of SEQ ID NO:4;and a second DNA segment encoding an additional polypeptide, wherein the first and second DNA segments are connected in-frame; and encode the fusion protein.

In another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 47 (Lys) to amino acid number 114 (Asp) of SEQ ID NO: 2; (b) the amino acid sequence as shown in SEQ ID NO:4 from amino acid number 1 (Met) to amino acid number 85 (Asp); (c) the amino acid sequence as shown in SEQ ID NO:3 from amino acid number 1 (Met) to amino acid number 89 (Asp); (d) the amino acid sequence as shown in SEQ ID NO:2 from amino acid residue number 1 (Met) to amino acid residue number 114 (Asp). In one embodiment, the isolated polypeptide disclosed above consists of a sequence of amino acid residues that is at least 90% identical to an amino acid sequence as shown in SEQ ID NO:2 from amino acid number 47 (Lys) to amino acid number 114 (Asp). In another embodiment, the isolated polypeptide disclosed above is as shown in SEQ ID NO:2 from amino acid number 47 (Lys) to amino acid number 114 (Asp). In another embodiment, the isolated polypeptide disclosed above contains motifs 1 through 5.

In another aspect, the present invention provides, a method of producing a zsig45 polypeptide comprising: culturing a cell into which has been introduced an expression vector as disclosed above; and isolating the zsig45 polypeptide produced by the cell.

In another aspect, the present invention provides, a method of producing an antibody to zsig45 polypeptide comprising: inoculating an animal with a polypeptide selected from the group consisting of: (a) a polypeptide consisting of 9 to 67 amino acids, wherein the polypeptide is at least 90% identical to a contiguous sequence of amino acids in SEQ ID NO:2 from amino acid number 47 (Lys) to amino acid number 114 (Asp); and (b) a polypeptide consisting of the amino acid sequence of SEQ ID NO:2 from amino acid number 47 (Lys) to amino acid number 114 (Asp); and wherein the polypeptide elicits an immune response in the animal to produce the antibody; and isolating the antibody from the animal.

In another aspect, the present invention provides, an antibody produced by the method disclosed above, which binds to a zsig45 polypeptide. In one embodiment, the antibody disclosed above is a monoclonal antibody. In another aspect, the present invention provides, an antibody which binds to a polypeptide disclosed above.

In another aspect, the present invention provides, a method of detecting, in a test sample, the presence of an antagonist of zsig45 protein activity, comprising: transfecting a zsig45-responsive cell, with a reporter gene construct that is responsive to a zsig45-stimulated cellular pathway; and producing a zsig45 polypeptide by the method disclosed above; and adding the zsig45 polypeptide to the cell, in the presence and absence of a test sample; and comparing levels of response to the zsig45 polypeptide, in the presence and absence of the test sample, by a biological or biochemical assay; and determining from the comparison, the presence of the antagonist of zsig45 activity in the test sample.

In another aspect, the present invention provides, a method of detecting, in a test sample, the presence of an agonist of zsig45 protein activity, comprising: transfecting a zsig45-responsive cell, with a reporter gene construct that is responsive to a zsig45-stimulated cellular pathway; and adding a test sample; and comparing levels of response in the presence and absence of the test sample, by a biological or biochemical assay; and determining from the comparison, the presence of the agonist of zsig45 activity in the test sample.

These and other aspects of the invention will become evident upon reference to the following detailed description of the invention..

DETAILED DESCRIPTION OF THE INVENTION

Prior to setting forth the invention in detail, it is helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in genotypic and phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5° CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multipeptide structure comprising an extracellular ligand-binding domain and an intracellular effector domain that is typically involved in signal transduction. Most nuclear receptors also exhibit a multi-domain structure, including an amino-terminal, transactivating domain, a DNA binding domain, and a ligand binding domain. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequences. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Teachings of all references cited herein are in their entirety incorporated by reference.

The present invention is based in part upon the discovery of a novel DNA sequence that encodes a polypeptide having a secretory signal sequence. Analysis of the tissue distribution of the mRNA corresponding to this novel cDNA showed that expression was restricted mainly to the thyroid. Expression was also evident in the pituitary and colon. This tissue-specific expression indicates a role in thyroid function. The polypeptide has been designated zsig45. The novel zsig45 polypeptides of the present invention were initially identified by querying an EST database for secretory signal sequences in an effort to select for secreted proteins. These sequences are characterized by an upstream methionine start site, a hydrophobic region of approximately 13 amino acids, and a cleavage site. Polypeptides corresponding to ESTs meeting these search criteria were compared to known sequences to identify secreted proteins having homology to known ligands. A single EST sequence was isolated and predicted to be a secreted protein. The novel polypeptide encoded by the full length cDNA has no apparent homolog relationship to known proteins, suggesting a completely novel protein that may be a member of a new protein family. Moreover, the signal sequence, predicted small size (8 kD, without post-translational modification), tissue-specific expression, certain novel motifs disclosed herein, and lack of long hydrophobic segments in the mature protein, suggests a small secreted molecule with potential as a new class of secreted cytokine-like or protein hormone-like molecules.

The nucleotide sequence of a representative zsig45-encoding DNA is described in SEQ ID NO. 1, and its deduced amino acid sequence is described in SEQ ID NO. 2. Analysis of the DNA encoding a zsig45 polypeptide (SEQ ID NO:1) revealed an open reading frame encoding 114 amino acids (SEQ ID NO:2) comprising a signal peptide of 46 amino acid residues (residue 1 (Met), to residue 46 (Ala) of SEQ ID NO:2) and a mature polypeptide of 68 amino acids (residue 47 (Lys) to residue 114 (Asp) of SEQ ID NO:2).

Analysis of the DNA encoding a zsig45 polypeptide (SEQ ID NO:1) also revealed three potential Methionine start residues that would enable translation initiation. The first is amino acid residue 1, the second is amino acid residue 26, and the third is amino acid residue 30 (See, SEQ ID NO:2). Thus, in addition to the first open reading frame disclosed above, there are two other open reading frames (ORFs) encoded by the same polynucleotide. These ORFs would encode the same mature polypeptide disclosed above. Analysis of the DNA encoding the zsig45 polypeptide (SEQ ID NO:2) revealed a second open reading frame encoding 89 amino acids (SEQ ID NO:3) containing a signal peptide of 21 amino acid residues (residue 1 (Met), to residue 21 (Ala) of SEQ ID NO:3), and a third open reading frame encoding 85 amino acids (SEQ ID NO:4) containing a signal peptide of 17 amino acid residues (residue 1 (Met), to residue 17 (Ala) of SEQ ID NO:4).

In proteins, regions of low variance (e.g., hydrophobic clusters) are often conserved in regions of structural importance (Sheppard, P., et al., Gene 150:163–167, 1994). Such regions of low variance often contain rare or infrequent amino acids, such as Tryptophan. Examining the low variance regions of zsig45 revealed the following five small regions of predicted conserved amino acids, referred to hereinafter as motifs 1 through 5: motif 1 (SEQ ID NO:5; corresponding to amino acids 50 to 56 of SEQ ID NO:2); motif 2 (SEQ ID NO:6; corresponding to amino acids 61 to 66 of SEQ ID NO:2); motif 3 (SEQ ID NO:7; corresponding to amino acids 71 to 76 of SEQ ID NO:2); motif 4 (SEQ ID NO:8; corresponding to amino acids 87 to 92 of SEQ ID NO:2); and motif 5 (SEQ ID NO:9; corresponding to amino acids 95 to 100 of SEQ ID NO:2).

The presence of conserved or low variance motifs generally correlates with or defines important structural regions in proteins. The regions between such motifs may be more variable, but are often functionally significant because they may relate to or define important structures and activities such as binding domains, biological and enzymatic activity, signal transduction, cell-cell interaction, tissue localization domains and the like.

The highly conserved amino acids in motifs 1 through 5 of zsig45 can be used as a tool to identify new family members. For instance, reverse transcription-polymerase chain reaction (RT-PCR) can be used to amplify sequences encoding the conserved motifs from RNA obtained from a variety of tissue sources or cell lines. In particular, highly degenerate oligonucleotide primers designed from the following zsig45 amino acid sequences of motifs 1 through 5 are useful for this purpose:

a) QEEGDP (motif 1; SEQ ID NO:5), corresponding to degenerate polynucleotides of SEQ ID NO:10 and their complement;

b) AMPYWP (motif 2; SEQ ID NO:6), corresponding to degenerate polynucleotides of SEQ ID NO:11 and their complement;

c) DFWNYV (motif 3; SEQ ID NO:7), corresponding to degenerate polynucleotides of SEQ ID NO:12 and their complement;

d) QIEDMA (motif 4; SEQ ID NO:8), corresponding to degenerate polynucleotides of SEQ ID NO:13 and their complement; and e) FFAHFP (motif 5; SEQ ID NO:9), corresponding to degenerate polynucleotides of SEQ ID NO:14 and their complement.

The corresponding polynucleotides encoding the zsig45 polypeptide regions, domains, motifs, residues and sequences described above are as shown in SEQ ID NO:1.

SEQ ID NO:15 is a degenerate polynucleotide sequence that encompasses all polynucleotides that encode the zsig45 polypeptide of SEQ ID NO:2 (amino acids 1–114). Thus, zsig45 polypeptide-encoding polynucleotides ranging from nucleotide 1 or 141 to nucleotide 342 of SEQ ID NO:15 are contemplated by the present invention. Also contemplated by the present invention are fragments and fusions as described herein with respect to SEQ ID NO:2, SEQ ID NO:3 and SEQ ID NO:4, which are formed from analogous regions of SEQ ID NO:15. The symbols in SEQ ID NO:15 are summarized in Table 1 below.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:15, encompassing all possible codons for a given amino acid, are set forth in Table 2 below.

TABLE 2

| Amino Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |

TABLE 2-continued

| Amino Acid | Letter | Codons | Degenerate Codon |
|---|---|---|---|
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2, SEQ ID NO:3 or SEQ ID NO:4. Such variant sequences can be tested for functionality as disclosed herein.

One of ordinary skill in the art will also appreciate that different species can exhibit "preferential codon usage." In general, see, Grantham, et al., *Nuc. Acids Res.*, 8:1893–1912, 1980; Haas, et al. *Curr. Biol.*, 6:315–324, 1996; Wain-Hobson, et al., *Gene*, 13:355–364, 1981; Grosjean, H., and Fiers, W., *Gene*, 18:199–209, 1982; Holm, L., *Nuc. Acids Res.*, 14:3075–3087, 1986; and Ikemura, T., *J. Mol. Biol.*, 158:573–597, 1982. As used herein, the terms "preferential codon usage" and "preferential codons" are terms of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:15 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Suitable stringent hybridization conditions are equivalent to about a 5 h to overnight incubation at about 42° C. in a solution comprising: about 40–50% formamide, up to about 5×SSC, about 5×Denhardt's solution, up to about 10% dextran sulfate, and about 10–20 µg/ml denatured commercially-available carrier DNA; hybridization is then followed by washing filters in up to about 2×SSC. For example, a suitable wash stringency is equivalent to 0.1×SSC to 2×SSC, 0.1% SDS, at 55° C. to 65° C. Stringent hybridization and wash conditions depend on the length of the probe, reflected in the $T_m$, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zsig45 RNA. Such tissues and cells are identified by Northern blotting (Thomas, *Proc. Natl. Acad. Sci. USA* 77:5201, 1980), and include thyroid, although DNA can also be prepared using RNA from other tissues or cell lines or isolated as genomic DNA. Total RNA can be prepared using guanidinium isothiocyanate extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding zsig45 polypeptides are then identified and isolated by, for example, hybridization or PCR.

A full-length clone encoding zsig45 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zsig45, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. Each internal section of the gene has complementary 3' and 5' terminal extensions designed to base pair precisely with an adjacent section. Thus, after the gene is assembled, process is completed by sealing the nicks along the backbones of the two strands with T4 DNA ligase. In addition to the protein coding sequence, synthetic genes can be designed with terminal sequences that facilitate insertion into a restriction endonuclease site of a cloning vector.

An alternative way to prepare a full-length gene is to synthesize a specified set of overlapping oligonucleotides (40 to 100 nucleotides). After the 3' and 5' short overlapping complementary regions are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from humans (paralogs) and from other species (orthologs). These species include, but are not limited to, mammalian, avian, amphibian, reptile, fish, insect and other vertebrate and invertebrate species. Of particular interest are zsig45 human paralogs and polypeptides from other mammalian species, including murine, rat, porcine, ovine, bovine, canine, feline, equine and other primate proteins. Species homologs of the human polypeptides. Orthologs of human zsig45 can be cloned using information and compositions provided by the present invention in combination with conventional cloning techniques. For example, a cDNA can be cloned using mRNA obtained from a tissue or cell type that expresses zsig45 as disclosed herein. Suitable sources of mRNA can be identified by probing Northern blots with probes designed from the sequences disclosed herein. A library is then prepared from mRNA of a positive tissue or cell line. A zsig45-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zsig45 sequence disclosed herein. Within an additional method, the cDNA library can be used to transform or transfect host cells, and expression of the cDNA of interest can be detected with an antibody to zsig45 polypeptide. Similar techniques can also be applied to the isolation of genomic clones.

Those skilled in the art will recognize that the sequence disclosed in SEQ ID NO:1, SEQ ID NO:2, SEQ ID NO:3 and SEQ ID NO:4 represent a single allele of the human zsig45 gene and polypeptide, and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:3 and SEQ ID NO:4.

cDNAs generated from alternatively spliced mRNAs, which retain the properties of the zsig45 polypeptide are included within the scope of the present invention, as are polypeptides encoded by such cDNAs and mRNAs. Allelic variants and splice variants of these sequences can be cloned by probing cDNA or genomic libraries e.g. a human thyroid cDNA library, from different individuals or tissues according to standard procedures known in the art.

The present invention also provides isolated zsig45 polypeptides that are substantially homologous to the polypeptides of SEQ ID NO:2, SEQ ID NO:3 and SEQ ID NO:4 and their human paralogs or species orthologs. The term "substantially similar" is used herein to denote polypeptides having 50%, preferably 60%, more preferably at least 80%, sequence identity to the sequences shown in SEQ ID NO:2 or their paralogs or orthologs. Such polypeptides will more preferably be at least 90% identical, and most preferably 95% or more identical to SEQ ID NO:2, SEQ ID NO:3, or SEQ ID NO:4 or its paralogs or orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.; New England Biolabs, Beverly, Mass.). The present invention thus includes polypeptides of from about 60 to about 150 amino acid residues that comprise a sequence that is at least 80%, preferably at least 90%, and more preferably 95% or more identical to the corresponding region of SEQ ID NO:2. Polypeptides comprising affinity tags can further comprise a proteolytic cleavage site between the zsig45 polypeptide and the affinity tag. Preferred such sites include thrombin cleavage sites and factor Xa cleavage sites.

TABLE 4

| Conservative amino acid substitutions | |
| --- | --- |
| Basic: | arginine |
|  | lysine |
|  | histidine |
| Acidic: | glutamic acid |
|  | aspartic acid |

TABLE 3

|  | A | R | N | D | C | Q | E | G | H | I | L | K | M | F | P | S | T | W | Y | V |
| --- | --- | --- | --- | --- | --- | --- | --- | --- | --- | --- | --- | --- | --- | --- | --- | --- | --- | --- | --- | --- |
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Variant zsig45 polypeptides or substantially homologous zsig45 polypeptides are characterized as having one or more amino acid substitutions, deletions or additions. These changes are preferably of a minor nature, that is conservative TABLE 4-continued Conservative amino acid substitutions

| | |
|---|---|
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zsig45 amino acid residues.

Essential amino acids in the zsig45 polypeptides of the present invention can be identified according to procedures known in the art, such as site-directed mutagenesis or alanine-scanning mutagenesis (Cunningham and Wells, *Science* 244: 1081–1085, 1989; Bass et al., *Proc. Natl. Acad. Sci. USA* 88:4498–502, 1991). In the latter technique, single alanine mutations are introduced at every residue in the molecule, and the resultant mutant molecules are tested for biological or biochemical activity (e.g., in situ localization or expression of zsig45; secretion followed by detection by antibodies; or activity measured by a signal transduction type assay) as disclosed below to identify amino acid residues that are critical to the activity of the molecule. See also, Hilton et al., *J. Biol. Chem.* 271:4699–4708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related family members.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zsig45 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., secreted and detected by antibodies; or measured by a signal transduction type assay) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptides that are substantially homologous to SEQ ID NO:2, SEQ ID NO:3, SEQ ID NO:4 or allelic variants thereof and retain the functional and structural properties of the wild-type protein. For example, using the methods described above, one could identify a receptor binding domain on zsig45; an extracellular ligand-binding domain of a receptor for zsig45; heterodimeric and homodimeric binding domains; other functional or structural domains; affinity tags; or other domains important for protein-protein interactions or signal transduction. Such polypeptides may also include additional polypeptide segments, such as affinity tags, as generally disclosed above.

The present invention further provides a variety of other polypeptide fusions and related multimeric proteins comprising one or more polypeptide fusions. For example, a zsig45 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin zsig45 polypeptide fusions can be expressed in genetically engineered cells to produce a variety of multimeric zsig45 analogs. Auxiliary domains can be fused to zsig45 polypeptides to target them to specific cells, tissues, or macromolecules (e.g., collagen). For example, a zsig45 polypeptide or protein could be targeted to a predetermined cell type by fusing a zsig45 polypeptide to a ligand that specifically binds to a receptor on the surface of the target cell. In this way, polypeptides and proteins can be targeted for therapeutic or diagnostic purposes. A zsig45 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

For any zsig45 polypeptide, including variants and fusion proteins, one of ordinary skill in the art can readily generate a fully degenerate polynucleotide sequence encoding that variant using the information set forth in Tables 1 and 2 above.

The zsig45 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zsig45 polypeptide of the present invention is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig45 polypeptide into the secretory pathway of a host cell, a secretory signal sequence (also known as a secretory peptide, leader sequence, prepro sequence or pre sequence) is provided in the expression vector. The secretory signal sequence may be that of the zsig45 polypeptide, or may be derived from another secreted protein (e.g., t-PA) or synthesized de novo. The secretory signal sequence is operably linked to the zsig45 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such signal fusion polypeptides. A DNA construct encoding a signal fusion polypeptide can be made wherein a signal sequence encoding a secretory peptide derived from any one of the three ORFs disclosed in SEQ ID NO:2 (amino acids 1 through 46 of SEQ ID NO:2), SEQ ID NO:3 (amino acids 1 through 21 of SEQ ID NO:3), or SEQ ID NO:4 (amino acids 1 through 17 of SEQ ID NO:4) and is operably linked to an another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J*. 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993), and viral vectors (A. Miller and G. Rosman, *BioTechniques* 7:980–90, 1989; Q. Wang and M. Finer, *Nature Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987 and WIPO publication WO 94/06463. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. The use of *Agrobacterium rhizogenes* as a vector for expressing genes in plant cells has been reviewed by Sinkar et al., *J. Biosci. (Bangalore)* 11:47–58, 1987.

Fungal cells, including yeast cells, and particularly cells of the genus Saccharomyces, can also be used within the present invention, such as for producing zsig45 polypeptides, zsig45 polypeptide fragments or polypeptide fusions. Methods for Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zsig45 baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zsig45 polypeptide into a baculovirus genome maintained in *E. coli* as a large plasmid called a "bacmid." See, Hill-Perkins, M. S. and Possee, R. D., *J Gen Virol* 71:971–6, 1990; Bonning, B. C. et al., *J Gen Virol* 75:1551–6, 1994; and, Chazenbalk, G. D., and Rapoport, B., *J Biol Chem* 270:1543–9, 1995. In addition, transfer vectors can include an in-frame fusion with DNA encoding an epitope tag at the C- or N-terminus of the expressed zsig45 polypeptide, for example, a Glu-Glu epitope tag (Grussenmeyer, T. et al., *Proc. Natl. Acad. Sci.* 82:7952–4, 1985). Using a technique known in the art, a transfer vector containing zsig45 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig45 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2$–$5\times10^5$ cells to a density of $1$–$2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the zsig45 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. . 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig45 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zsig45 polypeptides (including chimeric or fusion zsig45 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding ligand or receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural and biological properties. For example, simple ion exchange chromatography and reverse-phase HPLC and/or gel permeation chromatography can be employed to purify a protein of this size and pI. Other methods may also be employed. For example, immobilized metal ion adsorption (IMAC) chromatography can be used to purify histidine-rich proteins, including those comprising polyhistidine tags. Briefly, a gel is first charged with divalent metal ions to form a chelate (E. Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., polyhistidine, maltose-binding protein, an immunoglobulin domain) may be constructed to facilitate purification.

Moreover, using methods described in the art, polypeptide fusions, or hybrid zsig45 proteins, are constructed using regions or domains of the inventive zsig45 polypeptide in combination with those of other human 2–19 family proteins (e.g. human 2–19, D87120, and murine EF-7), or heterologous proteins (Sambrook et al., ibid., Altschul et al., ibid., Picard. D. *Cur. Opin. Biology*, 5:511–515, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion polypeptides can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zsig45 of the present invention with the functionally equivalent domain(s) from another family member or heterologous protein. Such domains comprise but are not limited to the three disclosed secretory signal sequences, the mature protein, and conserved motifs. Such fusion proteins would be expected to have a biological functional profile that is the same or similar to polypeptides of the present invention or to the proteins to which they are fused, depending on the fusion constructed. Moreover, such fusion proteins may exhibit other properties as disclosed herein.

Standard molecular biological and cloning techniques can be used to swap the equivalent domains between the zsig45 polypeptide and those polypeptides to which they are fused. Generally, a DNA segment that encodes a domain of interest, e.g., a zsig45 domain described herein, is operably linked in frame to at least one other DNA segment encoding an additional polypeptide (for instance an analogous domain or region human 2–19 protein), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature polypeptide; or a DNA construct would encode from N-terminus to C-terminus a fusion protein comprising a signal polypeptide followed by regions comprising the motifs 1 through 5 in the order as they appear in the zsig45 polypeptide, or the equivalent regions from a heterologous protein, e.g. human 2–19, protein. Such fusion proteins can be expressed, isolated, and assayed for activity as described herein.

Zsig45 polypeptides or fragments thereof may also be prepared through chemical synthesis. Zsig45 polypeptides may be monomers or multimers; glycosylated or non-glycosylated; pegylated or non-pegylated; and may or may not include an initial methionine amino acid residue.

The activity of molecules of the present invention may be measured using a variety of assays that measure thyroid, cardiovascular and bone function. Of particular interest are metabolism, thyroid or pituitary hormone secretion, and bone resorption and formation assays. Such assays are well known in the art.

In view of the tissue distribution observed for this zsig45 polypeptide, agonists (including the natural receptor/substrate/cofactor/etc.) and antagonists have enormous potential in both in vitro and in vivo applications. The zsig45 polypeptide, fragment thereof, or compounds identified as zsig45 agonists, antagonists may be useful for promoting growth, proliferation or differentiation of various cell types in vitro and treatment of extrathyroid or thyroid disorders in vivo. For example, such compounds are useful as components of defined cell culture media, and may be used alone or in combination with other cytokines and hormones to replace serum that is commonly used in cell culture.

Within another embodiment, there is provided a method of identifying antagonists of zsig45 polypeptides, comprising providing cells responsive to a zsig45 polypeptide, culturing a first portion of the cells in the presence of a test compound, culturing a second portion of the cells in the absence of a test compound, and detecting an increase in a cellular response of the first portion of the cells as compared to the second portion of the cells. Within another embodiment, there is provided a method of identifying antagonists of zsig45 polypeptide, comprising providing cells responsive to a zsig45 polypeptide, culturing a first portion of the cells in the presence of zsig45 polypeptide, culturing a second portion of the cells in the presence of the zsig45 polypeptide and a test compound, and detecting a decrease in a cellular response of the second portion of the cells as compared to the first portion of the cells.

Molecules of the present invention can be used to identify and isolate receptors involved in thyroid, pituitary, cardiac or other function, to which zsig45 polypeptides bind in vivo. For example, proteins and peptides of the present invention can be immobilized on a column and membrane preparations run over the column (*Immobilized Affinity Ligand Techniques*, Hermanson et al., eds., Academic Press, San Diego, Calif., 1992, 195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol* 33:1167–1180, 1984) and specific cell-surface proteins can be identified.

As a ligand, the activity of zsig45 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zsig45 polypeptide, its agonists, or antagonists. Preferably, the microphysiometer is used to measure responses of a zsig45-responsive eukaryotic cell, compared to a control eukaryotic cell that does not respond to zsig45 polypeptide. ZSIG45-responsive eukaryotic cells comprise cells into which a receptor for zsig45 has been transfected creating a cell that is responsive to zsig45; or cells naturally responsive to zsig45 such as cells derived from thyriod, heart, pituitary, hypothalmic, bone, bone marrow and skeletal muscle tissues amongst others. Differences, measured by a change, for example, an increase or diminution in extracellular acidification, in the response of cells exposed to zsig45 polypeptide, relative to a control not exposed to zsig45, are a direct measurement of zsig45-modulated cellular responses. Moreover, such zsig45-modulated responses can be assayed under a variety of stimuli. Using the microphysiometer, there is provided a method of identifying agonists of zsig45 polypeptide, comprising providing cells responsive to a zsig45 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Moreover, culturing a third portion of the cells in the presence of zsig45 polypeptide and the absence of a test compound can be used as a positive control for the zsig45-responsive cells, and as a control to compare the agonist activity of a test compound with that of the zsig45 polypeptide. Moreover, using the microphysiometer, there is provided a method of identifying antagonists of zsig45 polypeptide, comprising providing cells responsive to a zsig45 polypeptide, culturing a first portion of the cells in the presence of zsig45 and the absence of a test compound, culturing a second portion of the cells in the presence of zsig45 and the presence of a test compound, and detecting a change, for example, an increase or a diminution in a cellular response of the second portion of the cells as compared to the first portion of the cells. The change in cellular response is shown as a measurable change extracellular acidification rate. Antagonists and agonists, for zsig45 polypeptide, can be rapidly identified using this method.

Moreover, zsig45 can be used to identify cells, tissues, or cell lines which respond to a zsig45-stimulated pathway. The microphysiometer, described above, can be used to rapidly identify ligand-responsive cells, such as cells responsive to zsig45 of the present invention. Cells can be cultured in the presence or absence of zsig45 polypeptide. Those cells which elicit a measurable change in extracellular acidification in the presence of zsig45 are responsive to zsig45. Such cell lines, can be used to identify antagonists and agonists of zsig45 polypeptide as described above.

The polypeptides, nucleic acid and/or antibodies of the present invention may be used in treatment of disorders associated with thyroid dysfunction. The molecules of the present invention can be used to treat or prevent development of pathological conditions in such diverse tissue as thyroid, heart and bone. In particular, certain syndromes an diseases may be amenable to such diagnosis, treatment or prevention, such as thyroid disorders, ischemia reperfusion injury, inflammatory disorders, amongst others disclosed herein.

The activity of molecules of the present invention can be measured using a variety of assays that measure, for example, signal transduction upon binding a receptor, thyroid hormone secretion in vitro and in vivo, bone loss, TSH activity, or antibody binding. For example, zsig45 polypeptides can be labeled and tested for specific and saturating binding to specific cell lines or cells. Identification of positive cells to which zsig45 binds can be achieved by injecting a radioactively or fluorescently-labeled zsig45 polypeptide and using art-recognized immunohistochemistry methods to visualize a cell or tissue in vivo where zsig45 binds. After identification of positive cells to which zsig45 binds, activity can be tested for zsig45-mediated activation of a signal transduction pathway using methods known in the art. For instance, vector constructs containing a reporter (e.g. SRE-luciferase, STAT-luciferase, thyroid hormone response element (THRE)-luciferase or the like) can be introduced into the positive cell lines; such cell lines, when exposed to conditioned media containing secreted zsig45 protein, will demonstrate zsig45-mediated signal transduction activity through activation of the measurable reporter. Such assays are well known in the art. Specific assays include, but are not limited to, bioassays measuring signal transduction.

The molecules of the present invention may exert their effects in thyroid or extrathyroidally. Thus, activity of zsig45 polypeptides, agonists or antagonists, may affect thyroid function and can be measured by assessing thyroid hormone secretion in vitro or thyroid function in vivo. Thyroid hormones, and changes in thyroid hormone secretion in the presence or absence of zsig45, may be detected using various methods known in the art. For example, TSH and other thyroid hormones are commonly measured by radio-immune assay (RIA), immunometric assays (IMA) employing a "sandwich" type assay, or ELISA. Hormones, including T3 and T4, may be measured in vivo by a variety of methods known in the art (Elkins, R., *Endocr. Rev.*, 11:5–46, 1990). For example, T4 may be measured using a radiometric $^{125}$I binding assay, dialysis and ultrafiltration. See Braverman, L. E. (Ed.), ibid., p.35–48.

In addition, the zsig45 polypeptide, agonists or antagonists, of the present invention may modulate the plasma membrane protein, iodothyrone 5'-monodeiodinase type-II (5'D-II), which peripherally converts T4 to T3. Such effects can be measured indirectly in vivo by assessing T4 or T3 as discussed herein, or directly in vitro by measuring 5'D-II enzyme activity. Moreover, the effects of T3 clearance in liver by 5'-deiodinase type-I(5'D-I) can be assessed in vivo. See Braverman, L. E. (Ed.), ibid., p.49–68.

Moreover, in vivo affects of zsig45 polypeptides on thyroid function can also be assessed in experimental animals or humans by ultrasound, radioactive iodine uptake, and fine needle aspiration biopsy (Braverman, L. E. (Ed.), ibid., p.35–48).

Thyroid malfunction and some of the currently associated therapies can elicit detrimental effects on bone in vivo. Thus, given the thyroidal and pituitary localization of the present invention, assays that measure bone formation and/or resorption are important assays to assess zsig45 activity. One example is an assay system that permits rapid identification of substances having selective calcitonin receptor activity on cells expressing the calcitonin receptor. The calcitonin receptor is a member of the G-protein receptor family and transduces signal via activation of adenylate cyclase, leading to elevation of cellular cAMP levels (Lin et al., *Science* 254:1022–24, 1991). This assay system exploits the receptor's ability to elevate cAMP levels as a way to detect other molecules that are able to stimulate the calcitonin receptor and initiate signal transduction. Other assays that measure bone formation or resorption include calvarial assays, QCT, and assays that measure osteoblast size and number. Such assays are known in the art and discussed below.

Receptor activation can be detected by: (1) measurement of adenylate cyclase activity (Salomon et al., *Anal. Biochem.* 58:541–48, 1974; Alvarez and Daniels, *Anal. Biochem.* 187:98–103, 1990); (2) measurement of change in intracellular cAMP levels using conventional radioimmunoassay methods (Steiner et al., *J. Biol. Chem.* 247:1106–13, 1972; Harper and Brooker, *J. Cyc. Nucl. Res.* 1:207–18, 1975); or (3) through use of a cAMP scintillation proximity assay (SPA) method (Amersham Corp., Arlington Heights, Ill.). While these methods provide sensitivity and accuracy, they involve considerable sample processing prior to assay, are time consuming, involve the use of radioisotopes, and would be cumbersome for large scale screening assays.

An alternative assay system involves selection of polypeptides that are able to induce expression of a cyclic AMP response element (CRE)-luciferase reporter gene, as a consequence of elevated cAMP levels, in cells expressing a calcitonin receptor, but not in cells lacking calcitonin receptor expression, as described in U.S. Pat. Nos. 5,622,839, 5,674,689, and 5,674,981.

Well established animal models are available to test in vivo efficacy of zsig45 polypeptides, agonists or antagonists, that interact with the calcitonin receptor. Moreover, these models. may be used to test effects of zsig45 on bone other than through the calcitonin receptor. For example, the hypocalcemic rat or mouse model can be used to determine the effect on serum calcium, and the ovariectomized rat or mouse can be used as a model system for osteoporosis. Bone changes seen in these models and in humans during the early stages of estrogen deficiency are qualitatively similar. Calcitonin has been shown to be an effective agent for the prevention of bone loss in ovariectomized women and rats (Mazzuoli et al., *Calcif. Tissue Int.* 47:209–14, 1990; Wronski et al., *Endocrinology* 129:2246–50, 1991). High dose estrogen has been shown to inhibit bone resorption and to stimulate bone formation in an ovariectomized mouse model (Bain et al., *J. Bone Miner. Res.* 8:435–42, 1993).

Biologically active zsig45 polypeptides, agonists or antagonists, of the present invention that interact with the calcitonin receptor, or exert other effects on bone, are therefore contemplated to be advantageous for use in therapeutic applications for which calcitonin is useful. Such applications, for example, are in the treatment of osteoporosis, Paget's disease, hyperparathyroidism, osteomalacia, idiopathic hypercalcemia of infancy and other conditions. Additional applications are to inhibit gastric secretion in the treatment of acute pancreatitis and gastrointestinal disorders, and uses as analgesics, in particular for bone pain.

In vivo assays for measuring changes in bone formation rates include performing bone histology (see, Recker, R., eds. *Bone Histomorphometry: Techniques and Interpretation.* Boca Raton: CRC Press, Inc., 1983) and quantitative computed tomography (QCT; Ferretti, J. *Bone* 17:353S–364S, 1995; Orphanoludakis et al., *Investig. Radiol.* 14:122–130, 1979; and Durand et al., *Medical Physics* 19:569–573, 1992). An exemplary ex vivo assay for measuring changes in bone formation is a calavarial assay (Gowen et al., *J. Immunol.* 136:2478–2482, 1986) or resorption calvarial assay (Linkhart, T. A., and Mohan, S., *Endocrinology* 125:1484–1491, 1989).

In addition, polypeptides of the present invention can be assayed and used for their ability to modify inflammation. Methods to determine proinflammatory and antiinflammatory qualities of zsig45 are known in the art and discussed herein. For example, suppression of cAMP production is an indication of anti-inflammatory effects (Nihei, Y., et al., *Arch. Dermatol. Res.,* 287:546–552, 1995). Suppression of cAMP and inhibition of ICAM and HLA-Dr induced by IFN-γ in keratinocytes can be used to assess inhibition of inflammation. Alternatively, enhancement of cAMP production and induction of ICAM and HLA-Dr in this system can be an measurement of proinflammatory effects of a protein. Zsig45, likewise can exhibit similar inflammatory effects, as shown in vivo (Example 8) and may exert these effects in tissues in which it is expressed, or in other tissues. For example, zsig45 is expressed in the colon, and can be useful in promoting wound healing in this tissue, or exhibit antibacterial or anti-viral effects. Moreover, zsig45 or its antagonists can be useful in treatment of inflammatory bowel disease, diverticulitis, inflammation during and after intestinal surgery, and the like. In addition, zsig45, expressed in thyroid, can have wound-healing or antimicrobial or antiviral actions in tissues outside of thyroid, such, as heart, brain, liver, kidney, and the like. Moreover, direct measurement of zsig45 polypeptide and zsig45 antibodies can be useful in diagnosing inflammatory diseases such as melanoma, inflammatory bowel disease, diverticulitis, asthma, pelvic inflammatory disease, (PID), psoriasis, arthritis, reperfusion ischemia, and other inflammatory diseases. Moreover zsig45, antagonists can be useful in treatment of myocarditis, atherosclerosis, pelvic inflammatory disease, (PID), psoriasis, arthritis, eczema, scleroderma, and other inflammatory diseases.

As such, zsig45 polypeptide, agonists or its antagonists, have potential uses in inflammatory diseases such as asthma and arthritis. For example, if zsig45 is proinflammatory, antagonists would be valuable in asthma therapy or other anti-inflammatory therapies where migration of lymphocytes is damaging. In addition, zsig45 can serve other important roles in lung function, for instance, bronchodilation, tissue elasticity, recruitment of lymphocytes in lung infection and damage. Assays to assess the activity of zsig45 in lung cells are discussed in Laberge, S. et al., *Am. J. Respir. Cell Mol. Biol.* 17:193–202, 1997; Rumsaeng, V. et al., *J. Immunol.,* 159:2904–2910, 1997; and Schluesener, H. J. et al.,*J. Neurosci. Res.* 44:606–611, 1996. Methods to determine proinflammatory and antiinflammatory qualities of zsig45 its agonists or its antagonists are known in the art. Moreover, other molecular biological, immunological, and biochemical techniques known in the art and disclosed herein can be used to determine zsig45 activity and to isolate agonists and antagonists.

Moreover, based on high expression in thyriod, zsig45 polypeptide may exhibit antiviral activity by inhibiting viral replication by specific signaling via it's receptor(s) on a host cell (e.g. T-cell). Zsig45 can exhibit immune cell proliferative activity (See, example 8), can be assayed for this activity as disclosed herein, and may stimulate the immune system to fight viral infections. Moreover, zsig45 may bind CD4 or another lymphocyte receptor and exhibit antiviral effects, for example, against human immunodeficiency virus (HIV) or human T-cell lymphotropic virus (HTLV). Alternatively, zsig45 polypeptide may compete for a viral receptor or co-receptor to block viral infection. Zsig45 may be given parentally to prevent viral infection or to reduce ongoing viral replication and re-infection (Gayowski, T. et al., *Transplantation* 64:422–426, 1997). Thus, zsig45 may be used as an antiviral therapeutic, for example, for viral leukemias (HTLV), AIDS (HIV), or gastrointestinal viral infections caused by, for example, rotavirus, calicivirus (e.g., Norwalk Agent) and certain strains of pathogenic adenovirus.

Both zsig45 modulated direct and indirect inflammation can be assayed by methods in the art. Foe example see, Hamada, T. et al. *J. Exp. Med.* 188:539–548, 1998; and Liu, L. et al., *J. Immunol.* 161:3064–3070, 1998. For example, proinflammatory effects of zsig45 polypeptide can be directly tested in assays using a Transwell™ (Costar), wherein endothelial cells are plated on a semi-permeable membrane and zsig45 polypeptide is present in the lower chamber of the transwell and $Cr^{51}$ or fluorescently-labeled neutrophils (PMNs), lymphocytes, HL60 cells, K562 cells, or the like are added on to the upper chamber of the transwell. Migration of the PMNs and the like to the lower chamber of the transwell in the presence of zsig45 polypeptide, but not its absence (Negative control), would demonstrate zsig45 polypeptide as a direct chemoattractant of the PMNs. Moreover, IL-8 could be employed in this assay as a positive control. To test zsig45 as indirect stimulator of inflammatory response, a similar method can be employed. For example, an experiment can be set up as per above where in addition to the presence of zsig45 on the lower chamber of the transwell, fibroblast or adipocytes are plated there. In this way, effects of zsig45 polypeptide in inducing these cells to secrete factors that enhance migration of PMNs, i.e., inflammation, can be measured. The bFGF can be used as a positive control for indirect assay. Anti-inflammatory effects of zsig45 polypeptide can also be measured when added on the upper chamber in the presence of PMN's using a similar transwell assay known in the art.

The activity of molecules of the present invention may be measured using a variety of assays that, for example, measure neogenesis or hyperplasia (i.e., proliferation) of cardiac cells based on the potential effects of extrathyroidal activity of zsig45. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured using cultured cardiac cells or in vivo by administering molecules of the present invention to the appropriate animal model. Generally, proliferative effects are seen as an increase in cell number, and may include inhibition of apoptosis as well as stimulation of mitogenesis. Cultured cells for use in these assays include cardiac fibroblasts, cardiac myocytes, skeletal myocytes, and human umbilical vein endothelial cells from primary cultures. Suitable established cell lines include: NIH 3T3 fibroblasts (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992), and LNCap.FGC adenocarcinoma cells (ATCC No. CRL-1740.) Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabeled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. The novel polypeptides of the present invention may be useful for studies to isolate mesenchymal stem cells and cardiac myocyte progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of myocytes, smooth muscle cells, osteoblasts, adipocytes, chrondrocytes and endothelial cells. Molecules of the present invention may, while stimulating proliferation or differentiation of cardiac myocytes, inhibit proliferation or differentiation of adipocytes, by virtue of the affect on their common precursor/stem cells. Thus molecules of the present invention may have use in inhibiting chondrosarcomas, atherosclerosis, restenosis and obesity.

Assays measuring differentiation include, for example, measuring cell-surface markers associated with stage-specific expression of a tissue, enzymatic activity, functional activity or morphological changes (Watt, *FASEB,* 5:281–284, 1991; Francis, *Differentiation* 57:63–75, 1994; Raes, *Adv. Anim. Cell Biol. Technol. Bioprocesses,* 161–171, 1989; all incorporated herein by reference).

In vivo assays for evaluating cardiac neogenesis or hyperplasia include treating neonatal and mature rats with the molecules of the present invention. The animals' cardiac function is measured as heart rate, blood pressure, and cardiac output to determine left ventricular function. Post-mortem methods for assessing cardiac decline or improvement include: increased or decreased cardiac weight, nuclei/cytoplasmic volume, and staining of cardiac histology sections to determine proliferating cell nuclear antigen (PCNA) vs. cytoplasmic actin levels (Quaini et al., *Circulation Res.* 75:1050–1063, 1994 and Reiss et al., *Proc. Natl. Acad. Sci.* 93:8630–8635, 1996.)

Zsig45 polypeptides can also be used to prepare antibodies that specifically bind to zsig45 epitopes, peptides or polypeptides. The zsig45 polypeptide or a fragment thereof serves as an antigen (immunogen) to inoculate an animal and elicit an immune response. One of skill in the art would recognize that antigens or immunogenic epitopes can consist of stretches of amino acids within a longer polypeptide from less than about 10 amino acids or longer, and up to about the entire length of the polypeptide or longer depending on the polypeptide. Suitable antigens include the zsig45 polypeptide encoded by SEQ ID NO:2 from amino acid number 47 (Lys) to amino acid number 114 (Asp), or a contiguous 9 to 67 amino acid fragment thereof. Preferred peptides to use as antigens are hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored, or from the hydrophilic domains, motifs 1 through 5, or regions between motifs 1 through 5 disclosed herein. Antibodies generated from this immune response can be isolated and purified as described herein. Methods for preparing and isolating polyclonal and monoclonal antibodies are well known in the art. See, for example, *Current Protocols in Immunolocy*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, antibodies can be generated from inoculating a variety of warm-blooded animals such as horses, cows, goats, sheep, dogs, chickens, rabbits, mice, and rats with a zsig45 polypeptide or a fragment thereof. The immunogenicity of a zsig45 polypeptide may be increased through the use of an adjuvant, such as alum (aluminum hydroxide) or Freund's complete or incomplete adjuvant. Polypeptides useful for immunization also include fusion polypeptides, such as fusions of zsig45 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to zsig45 protein or peptide, and selection of antibody display libraries in phage or similar vectors (for instance, through use of immobilized or labeled zsig45 protein or peptide). Genes encoding polypeptides having potential zsig45 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zsig45 sequences disclosed herein to identify proteins which bind to zsig45. These "binding proteins" which interact with zsig45 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zsig45 "antagonists" to block zsig45 binding and signal transduction in vitro and in vivo. These anti-zsig45 binding proteins would be useful for inhibiting inflammation or other zsig45 activity.

Antibodies are determined to be specifically binding if: 1) they exhibit a threshold level of binding activity, and/or 2) they do not significantly cross-react with related polypeptide molecules. First, antibodies herein specifically bind if they bind to a zsig45 polypeptide, peptide or epitope with an affinity at least 10-fold greater than the binding affinity to control (non-zsig45) polypeptide. It is preferred that the antibodies exhibit a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect zsig45 but not known related polypeptides using a standard Western blot analysis (Ausubel et al., ibid.). Examples of known related polypeptides are orthologs, proteins from the same species that are members of a protein family (e.g. IL-16), zsig45 polypeptides, and non-human zsig45. Moreover, antibodies may be "screened against" known related polypeptides to isolate a population that specifically binds to the inventive polypeptides. For example, antibodies raised to zsig45 are adsorbed to related polypeptides adhered to insoluble matrix; antibodies specific to zsig45 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984.

A variety of assays known to those skilled in the art can be utilized to detect antibodies which specifically bind to zsig45 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zsig45 protein or polypeptide.

Antibodies to zsig45 may be used for tagging cells that express zsig45; for isolating zsig45 by affinity purification; for diagnostic assays for determining circulating levels of zsig45 polypeptides; for detecting or quantitating soluble zsig45 as marker of underlying pathology or disease; in analytical methods employing FACS; for screening expression libraries; for generating anti-idiotypic antibodies; and as neutralizing antibodies or as antagonists to block zsig45 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zsig45 or fragments thereof may be used in vitro to detect denatured zsig45 or fragments thereof in assays, for example, Western Blots or other assays known in the art.

Molecules of the present invention can be used to identify and isolate receptors involved in thyroid, pituitary, cardiac or other function, to which zsig45 polypeptides bind in vivo. For example, proteins and peptides of the present invention can be immobilized on a column and membrane preparations run over the column (*Immobilized Affinity Ligand Techniques*, Hermanson et al., eds., Academic Press, San Diego, Calif., 1992, pp. 195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Moreover, methods described above may be used to isolate anti-zsig45 binding proteins. Such antagonists can be isolated and used for treatment, for example, in rhabdomyosarcoma, cardiac myxoma, bone cancers of osteoblast origin, and dwarfism, arthritis, ligament and cartilage repair, alone or combination with other therapies.

The molecules of the present invention may be useful for elucidation and prevention of various thyroid diseases, bone diseases, menstrual problems, heart diseases, bone, colon, pituitary and thyroid cancers. The polypeptides, nucleic acid and/or antibodies of the present invention may be used in treatment of disorders associated with thyroid dysfunction. The molecules of the present invention may used to modulate thyroid activity or to treat or prevent development of pathological conditions in such diverse tissue as thyroid, heart and bone. In particular, certain syndromes and diseases may be amenable to such diagnosis, treatment or prevention.

The present invention also provides methods of studying mammalian cellular metabolism. Such methods of the present invention comprise incubating cells to be studied, for example, human vascular endothelial cells, ±zsig45 polypeptide, monoclonal antibody, agonist or antagonist thereof and observing changes in adipogenesis, gluconeogenesis, glycogenolysis, lipogenesis, glucose uptake, or the like.

Within another aspect of the present invention there is provided a pharmaceutical composition comprising a purified zsig45 polypeptide in combination with a pharmaceutically acceptable vehicle. This pharmaceutical composition may be used to modulate energy balance in mammals or to protect endothelial cells from injury.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zsig45 polypeptides or anti-zsig45 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zsig45-cytokine fusion proteins or antibody-cytokine fusion proteins can be used for enhancing in vivo killing of target tissues (for example, blood and bone marrow cancers), if the zsig45 polypeptide or anti-zsig45 antibody targets the hyperproliferative blood or bone marrow cell (See, generally, Hornick et al., *Blood* 89:4437–47, 1997). Hornick et al. described fusion proteins enable targeting of a cytokine to a desired site of action, thereby providing an elevated local concentration of cytokine. Suitable zsig45 polypeptides or anti-zsig45 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, the zsig45 polypeptide or anti-zsig45 antibody can target vascular cells or tissues. Such polypeptide or antibody can be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Moreover, methods described above may be used to isolate anti-zsig45 binding proteins. Such antagonists can be isolated and used for treatment, for example, in rhabdomyosarcoma, cardiac myxoma, bone cancers of osteoblast origin, and dwarfism, arthritis, ligament and cartilage repair, alone or combination with other therapies.

The molecules of the present invention may be useful for elucidation and prevention of various thyroid diseases, inflammation, bone diseases, menstrual problems, heart diseases, bone, colon, pituitary and thyroid cancers. n may used to modulate thyroid Polynucleotides encoding zsig45 polypeptides are useful within gene therapy applications where it is desired to increase or inhibit zsig45 activity. If a mammal has a mutated or absent zsig45 gene, the zsig45 gene can be introduced into the cells of the mammal. In one embodiment, a gene encoding a zsig45 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, retroviruses, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zsig45 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zsig45 gene transcription, such as to inhibit cell proliferation in vivo. Polynucleotides that are complementary to a segment of a zsig45-encoding polynucleotide (e.g., a polynucleotide as set forth in SEQ ID NO:1) are designed to bind to zsig45-encoding mRNA and to inhibit translation of such mRNA. Such antisense polynucleotides are used to inhibit expression of zsig45 polypeptide-encoding genes in cell culture or in a subject.

Mice engineered to express the zsig45 gene, referred to as "transgenic mice," and mice that exhibit a complete absence of zsig45 gene function, referred to as "knockout mice," may also be generated (Snouwaert et al., *Science* 257:1083, 1992; Lowell et al., *Nature* 366:740–42, 1993; Capecchi, M. R., Science 244: 1288–1292, 1989; Palmiter, R. D. et al. *Annu Rev Genet.* 20: 465–499, 1986). For example, transgenic mice that over-express zsig45, either ubiquitously or under a tissue-specific or tissue-restricted promoter can be used to ask whether over-expression causes a phenotype. For example, over-expression of a wild-type zsig45 polypeptide, polypeptide fragment or a mutant thereof may alter normal cellular processes, resulting in a phenotype that identifies a tissue in which zsig45 expression is functionally relevant and may indicate a therapeutic target for the zsig45, its agonists or antagonists. For example, a preferred transgenic mouse to engineer is one that over-expresses the mature zsig45 polypeptide. Moreover, such over-expression may result in a phenotype that shows similarity with human diseases. Similarly, knockout zsig45 mice can be used to determine where zsig45 is absolutely required in vivo. The phenotype of knockout mice is predictive of the in vivo effects of that a zsig45 antagonist, such as those described herein, may have. The human zsig45 cDNA can be used to isolate murine zsig45 mRNA, cDNA and genomic DNA, which are subsequently used to generate knockout mice. These mice may be employed to study the zsig45 gene and the protein encoded thereby in an in vivo system, and can be used as in vivo models for corresponding human diseases. Moreover, transgenic mice expression of zsig45 antisense polynucleotides or ribozymes directed against zsig45, described herein, can be used analogously to knockout mice described above.

Other diagnostic applications using zsig45 can be employed. For example, the zsig45 gene, a probe comprising zsig45 DNA or RNA or a subsequence thereof can be used to determine if the zsig45 gene is expressed differently in diseased tissues. For example, among other diseases, zsig45 may be expressed in certain pancreatic, prostatic, intestinal, throat and lung cancers, or other diseases associated with those tissues. In the alternative, zsig45 expression in certain tissues may be decreased in certain disease states relative to normal.

With regard to modulating energy balance, zsig45 polypeptides may be used to modulate cellular metabolic reactions. Such metabolic reactions include adipogenesis, gluconeogenesis, glycogenolysis, lipogenesis, glucose uptake, protein synthesis, thermogenesis, oxygen utilization and the like. The expression pattern of zsig45 polypeptide indicates expression in a major metabolic organ, thyroid, and may have intra- and extrathyroidal effects on endothelial cell tissues. Such effects involve protection, regeneration, growth and development of thyroidal or other tissues.

With regard to endothelial cell protection, zsig45 polypeptides may be used in organ preservation, for cryopreservation, for surgical pretreatment to prevent injury due to ischemia and/or inflammation or in like procedures. In this regard, zsig45 polypeptides may find utility in modulating nutrient uptake, as demonstrated, for example, by 2-deoxy-glucose uptake in the brain or the like.

The zsig45 polypeptides may modulate mammalian energy balance. The thyroid expression pattern of zsig45 suggests that zsig45 may exhibit effects on glucose uptake, e.g. through GLUT-1, and thermogenesis (thermoregulation). Among other methods known in the art or described herein, mammalian energy balance may be evaluated by monitoring one or more of the following metabolic functions: adipogenesis, gluconeogenesis, glycogenolysis, lipogenesis, glucose uptake, protein synthesis, thermogenesis, oxygen utilization or the like. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogenolysis. In skeletal muscle and adipose tissue, insulin acts to stimulate the uptake, storage and utilization of glucose.

Zsig45 polypeptide is expressed in thyroid but may exhibit extrathyroidal activity in organs that affect metabolic functions. Thus, pharmaceutical compositions of the present invention may be useful in prevention or treatment of pancreatic disorders. For example, zsig45 may be associated with pathological regulation of the expansion of neurocrine and exocrine cells in the pancreas, as evident in IDDM, pancreatic cancer or the like. Pharmaceutical compositions of the present invention may also be involved in prevention or treatment of pancreatic conditions characterized by dysfunction associated with pathological regulation of blood glucose levels, insulin resistance or digestive function.

Art-recognized methods exist for monitoring all of the metabolic functions recited above. Thus, one of ordinary skill in the art is able to evaluate zsig45 polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation at the ob (obese) locus. Such ob/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except ob/db mice display a more severe diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^{3}$H or $^{14}$C-labeled deoxyglucose is added to $\geq$50 1 M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytochalasin b, an inhibitor of glucose transport. Other methods include those described by, for example, Manchester et al., *Am. J. Physiol.* 266 (*Endocrinol. Metab.* 29):E326-E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides*, W. Colmers and C. Wahlestedt (eds.), Humana Press, Ottawa, 1993, pp. 457–509; C. Billington et al., *Am. J. Physiol.* 260:R321, 1991; N. Zarjevski et al., *Endocrinology* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245(3):

R321–8, 1983. Also, metabolic rate, which may be measured by a variety of techniques, is an indirect measurement of thermogenesis.

Oxygen utilization may be evaluated as described by Heller et al., *Pflugers Arch* 369(1): 55–9, 1977. This method also involved an analysis of hypothalmic temperature and metabolic heat production. Oxygen utilization and thermoregulation have also been evaluated in humans as described by Haskell et al., *J. Appl. Physiol.* 51(4): 948–54, 1981.

The zsig45 polypeptides of the present invention may act in the neuroendocrine/exocrine cell fate decision pathway and is therefore capable of regulating the expansion of neuroendocrine and exocrine cells in the pancreas. One such regulatory use is that of islet cell regeneration. Also, it has been hypothesized that the autoimmunity that triggers IDDM starts in utero, and zsig45 polypeptide is a developmental gene involved in cell partitioning. Assays and animal models are known in the art for monitoring the exocrine/neuroendocrine cell lineage decision, for observing pancreatic cell balance and for evaluating zsig45 polypeptide, fragment, fusion protein, antibody, agonist or antagonist in the prevention or treatment of the conditions set forth above.

Among other methods known in the art or described herein, mammalian endothelial cell tissue protection may be evaluated by monitoring the function of endothelial tissue. For example, the function of the heart (aorta) may be evaluated by monitoring acetylcholine release, norepinephrine release or like parameters. These parameters are monitored by techniques (assays or animal models) known to one of ordinary skill in the art, as is more fully set forth below.

Acetylcholine and norepinephrine release may be monitored by HPLC. Levy, *Electrophysiology of the Sinoatrial and Atrioventricular Nodes,* Alan R. Liss, Inc., 187–197, 1998, describes measurement of norepinephrine in coronary sinus effluent. In addition, animals may be electrically paced, with the results monitored as described by Elsner, *European Heart Journal* 16(*Supplement N*) 52–8, 1995; and Reiffel and Kuehnert, *PACE* 17(*Part* 1): 349–65, 1994.

The zsig45 polypeptide is also expressed in the colon. Thus, zsig45 polypeptide pharmaceutical compositions of the present invention may also be useful in prevention or treatment of digestive disorders in the GI tract, such as disorders associated with pathological secretory cell expansion or differentiation. Assays and animal models are known in the art for monitoring such expansion or differentiation and for evaluating zsig45 polypeptides, including polypeptide fragments, fusion proteins, antibodies, agonists and antagonists in the prevention or treatment thereof.

Moreover, trefoil factors in the intestine are known to be involved in mucosal stabilization in the gut and repair processes associated with acute injury, particularly epithelial restitution (Poulsom, R., *Bail. Clin. Gastro.,* 10: 113–134, 1996; Sands, B. E., and Podolsky, D. K., *Annu. Rev. Physiol.,* 58: 253–273, 1996). Also, trefoil proteins appear to have a role in healing wounds caused by intestinal inflammatory diseases, and resisting microbial invasion via mucosal secretion involvement (Palut, A. G., *New Eng. J. Med.,* 336: 5-6-507, 1997; Playford, R. J., *J. Royal Coll. Phys. London,* 31: 37–41, 1997). Epidermal growth factor (EGF) receptor ligands may play a role in enhancing trefoil activity in the gut; however, repair of mucosal injury is not dependent on the main endogenous EGF receptor ligand in the gut, TNF-a, suggesting a role of other, undiscovered ligands (Cook, G. A., et al., *Am. Physiol. Soc.,* G1540–G1549, 1997). For example, the zsig45 polypeptides may serve as such ligand, regulatory protein or other factor in the trefoil pathway, and hence play an important therapeutic role in diseases and injury associated with the gut and mucosal epithelium.

EGF is also expressed in thyroid and modulates the growth and differentiation of thyroid cells in vitro (Dagogo-Jack, S., *Afr. J. Med. Sci.,* 24:211–217, 1995). Thus, interaction of zsig45 with EGF receptor may also affect thyroid function and hence play a therapeutic role in thyroid diseases, or diseases associated with thyroid malfunction. Many growth factors are detected in thyroid tissue (Dagogo-Jack, S., ibid.); zsig45 may affect on one or more of these other factors' activities or physiologic pathways.

Thyroid expression of zsig45 suggests that the polypeptides of the present invention may be analogous to known thyroid hormones by acting upon cell membranes of extrathyroidal tissues. Thus, the polypeptides of the present invention may exert non-nuclear effects on cell membranes and be useful in therapeutic applications in tissues such as heart and lymphoid tissues. For example, membrane effects may include inactivation of the myocardial $Na^+$-channel or stimulation of red cell $Ca^{2+}$-ATPase activity. Thus, zsig45 peptides of the present invention may be used in treatment of heart disease or malfunctions in myocardial contractility, or other diseases associated with solute transport and ion channels, such as kidney, bone marrow, muscular, heart and or neural pathologies associated with genetic and other human disease states, such as diabetes, bone disease, hematopoietic disorders, immune disorders, leukemias, hypertension, cardiac hypertrophy, other cardiac disorders and neural diseases.

The effects of thyroid function on cardiac function are well documented (Lompre, A., et al., *J. Mol. Cell Cardiol.,* 26:1109–1121, 1994). In animals, enhanced contraction and relaxation velocities are associated with hyperthyroidism, and decreased contractility is associated with hypothyroidism. These effects may be mediated through the $Ca^{2+}$-ATPase found in the myocardial sarcoplasmic reticulum. Such effects can readily be measured using assays disclosed below.

The cardiac activity of molecules of the present invention may be measured using a Langendorff assay. This preferred assay measures ex vivo cardiac function for an experimental animal, and is well known in the art. Experimental animals are, for example but not limited to, rats, rabbits and guinea pigs. Chronic effects on heart tissue can be measured after treating a test animal with zsig45 polypeptide for 1 to 7 days, or longer. Control animals will have only received buffer. After treatment, the heart is removed and perfused retrograde through the aorta. During perfusion, several physiologic parameters are measured: coronary blood flow per time, left ventricular (LV) pressures, and heart rate. These perameters directly reflect cardiac function. Changes in these parameters, as measured by the Langendorff assay, following in vivo treatment with zsig45 polypeptide relative to control animals indicates a chronic effect of the polypeptide on heart function. Moreover, the Langendorff assay can also be employed to measure the acute effects of zsig45 polypeptide on heart. In such application, hearts from untreated animals are used and zsig45 polypeptide is added to the perfusate in the assay. The parameters assessed above are measured and compared with the results from control hearts where zsig45 polypeptide was omitted from the perfusate. Differences in heart rate, change in pressure per time, and/or coronary blood flow indicate an acute effect of the molecules of the present invention on heart function.

The activity of molecules of the present invention may also be measured using a variety of assays that measure ion channel activity. Of particular interest is measuring ion transfer cross cell membranes. Such assays are well known in the art. Specific assays to assess the activity of novel ion channels or their regulators include, but are not limited to, bioassays measuring voltage-dependent conductance in *Xenopus laevis* oocytes (see, Rudy, B., Iverson, L. E., eds., *Meth. Enzymol.*, vol. 207, Academic Press, San Diego, Calif., 1992; Hamill, O. P et al., *Pfluegers Arch.* 391:85–100, 1981; Moorman, J. R. et al., *J. Biol. Chem.* 267:14551–14554, 1992; Durieux, M. E., et al., *Am. J. Physiol.* 263:C896–C900, 1992). This method involves injecting in vitro expressed mRNAs into isolated oocytes and assessing voltage-dependent conductance using a patch-clamp technique. An ion channel or its regulator may increase voltage-dependent conductance in this assay system. This system may be applied to other cell types, such as insect and mammalian cells (see, Rudy, B., Iverson, L. E., eds., ibid.). Other assays involve measuring ion channel activity indirectly in mammalian or other cell types, through the use of a chelator dye, such as Fura2 (See, for example, James-Kracke M. R., *J. Gen. Physiol.* 99:41–62, 1992; Raghu, P. et al., *Gene* 190:151–156, 1997). Ion channel activity can also be monitored by using a radiolabeled ion, such as a $^{125}$I efflux assay (Xia, Y. et al., *J. Membr. Biol.* 151:269–278, 1996). Other assays involve measuring changes in gene expression in mammalian cells signaled by ion flux or ion channel phosphorylation; for example, by driving expression of a measurable reporter gene, e.g. luciferase, under a suitable promoter as disclosed herein.

The molecules of the present invention may be useful for proliferation of cardiac tissue cells, such as cardiac myocytes or myoblasts; skeletal myocytes or myoblasts and smooth muscle cells; chrondrocytes; endothelial cells; adipocytes and osteoblasts in vitro. For example, molecules of the present invention are useful as components of defined cell culture media, and may be used alone or in combination with other cytokines and hormones to replace serum that is commonly used in cell culture. Molecules of the present invention are particularly useful in specifically promoting the growth and/or development of myocytes in culture, and may also prove useful in the study of cardiac myocyte hyperplasia and regeneration.

The polypeptides, nucleic acids and/or antibodies of the present invention may be used in treatment of disorders associated with myocardial infarction, congestive heart failure, hypertrophic cardiomyopathy and dilated cardiomyopathy. Molecules of the present invention may also be useful for limiting infarct size following a heart attack, aiding in recovery after heart transplantation, promoting angiogenesis and wound healing following angioplasty or endarterectomy, to develop coronary collateral circulation, for revascularization in the eye, for complications related to poor circulation such as diabetic foot ulcers, for stroke, following coronary reperfusion using pharmacologic methods, and other indications where angiogenesis is of benefit. Molecules of the present invention may be useful for improving cardiac function, either by inducing cardiac myocyte neogenesis and/or hyperplasia, by inducing coronary collateral development, or by inducing remodeling of necrotic myocardial area. Other therapeutic uses for the present invention include induction of skeletal muscle neogenesis and/or hyperplasia, kidney regeneration and/or for treatment of systemic and pulmonary hypertension.

zsig45 induced coronary collateral development is measured in rabbits, dogs or pigs using models of chronic coronary occlusion (Landau et al., *Amer. Heart J.* 29:924–931, 1995; Sellke et al., Surgery 120(2):182–188, 1996; and Lazarous et al., 1996, ibid.) Zsig45 efficacy for treating stroke is tested in vivo, in rats, utilizing bilateral carotid artery occlusion and measuring histological changes, as well as maze performance (Gage et al., *Neurobiol. Aging* 9:645–655, 1988). Zsig45 efficacy in hypertension is tested in vivo utilizing spontaneously hypertensive rats (SHR) for systemic hypertension (Marche et al., *Clin. Exp. Pharmacol. Physiol. Suppl.* 1:S114–116, 1995).

Polynucleotides of the present invention are also used to detect abnormalities on human chromosome 2 associated with disease or other human traits. The polynucleotides of the present invention map to the 2q37.3 region on human chromosome 2. The zsig45 gene maps 1086.2 cR_3000 from the top of the human chromosome 2 linkage group on the WICGR radiation hybrid map. Proximal and distal framework markers were WI-6310 (D2S2704) and D2S2585, respectively. The use of surrounding markers positions the zsig45 gene in the 2q37.3 region on the integrated LDB chromosome 2 map.

The present invention also provides reagents which will find use in diagnostic applications. For example, the zsig45 gene, a probe comprising zsig45 DNA or RNA, or a subsequence thereof, can be used to determine if the zsig45 gene is present on chromosome 2 or if a mutation has occurred. Detectable chromosomal aberrations at the zsig45 gene locus include but are not limited to aneuploidy, gene copy number changes, insertions, deletions, restriction site changes, and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel, et. al., ibid.; Marian, A. J., *Chest*, 108: 255–265, 1995).

Zsig45 polynucleotide probes can be used to detect abnormalities or genotypes associated with or located at 2q37.3, that manifest themselves in human disease states as well as map to this region of the human genome. See the Online Mendellian Inheritance of Man (OMIM) gene map, and references therein, for this region of chromosome 2 on a publicly available WWW server (http://www3.ncbi.nlm.nih.gov/htbin-post/Omim/getmap?chromosome=2q37.3). All of these that manifest themselves in human disease states serve as possible candidate genes for an inheritable disease which show linkage to the same chromosomal region as the zsig45 gene.

Similarly, defects in the zsig45 locus itself may result in a heritable human disease state. Molecules of the present invention, such as the polypeptides, antagonists, agonists, polynucleotides and antibodies of the present invention would aid in the detection, diagnosis prevention, and treatment associated with a zsig45 genetic defect.

Other diagnostic applications using zsig45 can be employed. For example, the zsig45 gene probe comprising zsig45 DNA or RNA, or a subsequence thereof, can be used to determine if the zsig45 gene is expressed differently in diseased tissues. Thus, such a zsig45 probe can be used to assess thyroid function. For example, among other diseases, zsig45 may be expressed in certain thyroid, pituitary, colon, bone and endocrine cancers, or other diseases associated with those tissues. In the alternative, zsig45 expression in certain tissues may be decreased in certain disease states relative to normal.

For pharmaceutical use, the polypeptides of the present invention are formulated for parenteral, particularly intravenous or subcutaneous, delivery according to conventional methods. Intravenous administration will be by bolus injection or infusion over a typical period of one to several hours. For applications for which local effects are preferred, such as for influencing the formation of certain types of mature cells from localized (e.g., thyroid) stem cells, formulations designed for local administration are preferred. Such pharmaceutical compositions are amenable, for example, to implantation or other local delivery method and may additionally be formulated for sustained release. Formulation of pharmaceutical compositions for a variety of modes of administration is within the level of ordinary skill in the art.

In general, pharmaceutical formulations will include a zsig45 polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be determined by the clinician according to accepted standards, taking into account the nature and severity of the condition to be treated, patient traits, etc. Determination of dose is within the Level of ordinary skill in the art. The polypeptides may be administered for acute treatment, over one week or less, often over a period of one to three days or may be used in chronic treatment, over several months or years.

The invention is further illustrated by the following non-limiting examples.

EXAMPLES

Example 1

Identification of zsig45

A. Using an EST Sequence to Obtain Full-length zsig45

Scanning of a translated in-house pituitary library DNA database using a signal trap as a query resulted in identification of an expressed sequence tag (EST) sequence found to be homologous to a human secretory signal sequence. Oligonucleotide primers were designed from the sequence of the identified EST. The primers were used for priming internally within the EST to isolate a full-length clone from the human pituitary cDNA library.

B. Isolation of Full Length zsig45 cDNA

To obtain a full-length cDNA, 3' RACE was employed. A 3' RACE product was generated using a human pituitary cDNA library as template and oligonucleotides ZC 694 (SEQ ID NO:16) and ZC 14,030 (SEQ ID NO:17) as primers. This first-round 3' RACE PCR reaction was run as follows: 1 cycle at 94° C. for 5 minutes; 35 cycles at 94° C. for 30 seconds, then 55° C. 30 seconds, then 72° C. for 3 minutes.

The resulting DNA products were electrophoresed on a 1.5% agarose gel, and a prominent band at approximately 650 bp was seen. The DNA band was gel purified and subcloned into a PCR-blunt™ vector (Invitrogen, San Diego, Calif.). Sequence analyses of the subclone revealed that the DNA products included the EST DNA sequence.

This 650 bp insert was liberated from the vector by restriction enzyme digestion with EcoRI and was electrophoresed on a 1% agarose gel. The fragment was purified using a commercially available gel extraction kit (QiaexII™; Qiagen Inc., Chatsworth, Calif.), and then radioactively labeled with $^{32}$P-dCTP using Prime-It II, a random prime labeling system (Stratagene Cloning Systems, La Jolla, Calif.), according to the manufacturer's specifications. The probe was then purified using a Nuc-Trap™ column (Stratagene) according to the manufacturer's instructions. ExpressHyb™ (Clontech, Palo Alto, Calif.) solution was used for prehybridization and as a hybridizing solution for colony lifts of the human pituitary library. Hybridization took place overnight at 65° C. using 5×10$^6$ cpm/ml of labeled probe. The colony lifts were then washed in 2×SSC/ 1% SDS at 65° C., followed by a wash in 0.1×SSC/0.1% SDS at 55° C. Hybridizing clones were isolated and discovered to contain a full-length cDNA encoding zsig45 protein.

Example 2

Tissue Distribution

Northern blot analysis was performed using Human Multiple Tissue Blots (MTN I, MTN II, and MTN III) (Clontech). The vector containing the 650 bp cloned insert described in Example 1 was restriction enzyme digested and electrophoresed on a 1% agarose gel. The 650 bp fragment was purified using a commercially available kit (QiaexII™; Qiagen) and then radioactively labeled with $^{32}$P-dCTP using Prime-It II, a random prime labeling system (Stratagene Cloning Systems), according to the manufacturer's specifications. The probe was then purified using a Nuc-Trap™ column (Stratagene) according to the manufacturer's instructions. ExpressHyb™ (Clontech) solution was used for prehybridization and as a hybridizing solution for the Northern blots. Hybridization took place overnight at 65° C. using 5×10$^6$ cpm/ml of labeled probe. The blots were then washed in 2×SSC/1% SDS at 65° C., followed by a wash in 0.1×SSC/0.1% SDS at 55° C. One transcript size was detected at approximately 650 bp. Signal intensity was highest for thyroid. No signals at 650 bp were present in any other tissues represented on the blots.

Dot Blots were also performed using Human RNA Master Blots™ (Clontech). The methods and conditions for the Dot Blots are the same as for the Multiple Tissue Blots disclosed above. Strong signal intensity was present in thyroid gland, and pituitary gland. Less intense signals were indicated in colon.

Example 3

PCR-Based Chromosomal Mapping of the zsig45 Gene

Zsig45 was mapped to chromosome 2 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/ rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zsig45 with the "GeneBridge 4 RH Panel", 20 μl reactions were set up in a 96-well microtiter plate (Stratagene, La Jolla, Calif.) and used in a "RoboCycler Gradient 96" thermal cycler (Stratagene). Each of the 95 PCR reactions consisted of 2 μl 10×KlenTaq PCR reaction buffer (Clontech), 1.6 μl dNTPs mix (2.5 mM each, Perkin-Elmer, Foster City, Calif.), 1 μl sense primer, ZC 15,414 (SEQ ID NO:18) 1 μl antisense primer, ZC 15,413 (SEQ ID NO:19), 2 μl "RediLoad" (Research Genetics, Inc.), 0.4 μl 50×Advantage KlenTaq Polymerase Mix (Clontech), 25 ng of DNA from an individual hybrid clone or control and ddH$_2$O for a total volume of 20 μl. The reactions were overlaid with an equal amount of mineral oil and sealed. The PCR cycler conditions were as follows: an initial 1 cycle 5 minute denaturation at 95° C. 40 cycles of a 1 minute denaturation at 95° C., 1 minute annealing at 62° C. and 1.5 minute. extension at 72° C.; followed by a final 1 cycle extension of 7 minutes at 72° C. The reactions were separated by electrophoresis on a 2% agarose gel (Life Technologies, Gaithersburg, Md.).

The results showed that zsig45 maps 1086.2 cR_3000 from the top of the human chromosome 2 linkage group on the WICGR radiation hybrid map. Proximal and distal framework markers were WI-6310 (D2S2704) and D2S2585,respectively. The use of surrounding markers positions zsig45 in the 2q37.3 region on the integrated LDB chromosome 2 map (The Genetic Location Database, University of Southhampton, www server: http://cedar.genetics. soton.ac.uk/public_html/).

Example 4

Construction and Expression of zsig45 Amino Terminal Glu-Glu Tagged and Carboxy Terminal Glu-Glu Tagged Yeast Expression Vectors Expression of zsig45 in *Pichia methanolica* utilizes the expression system described in co-assigned WIPO publication WO 97/17450. An expression plasmid containing all or part of a polynucleotide encoding zsig45 is constructed via homologous recombination. Expression vectors were built from pCZR204 to express a C-terminal Glu-Glu-tagged (CEE), or an N-terminal Glu-Glu-tagged (NEE) zsig45 polypeptide. The pCZR204 vector contains the AUG1 promoter, followed by the αFpp leader sequence, followed by an N-terminal Glu-Glu tag, a blunt-ended Sma I restriction site, a carboxy-terminal peptide tag (Glu-Glu), a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. The zsig45 sequence inserted into these vectors begins at residue 47 (Lys) of the zsig45 amino acid sequence (SEQ ID NO:2).

For each construct two linkers are prepared, and along with zsig45, were homologously recombined into the yeast expression vectors described above. The untagged N-terminal linker (SEQ ID NO:20) spans 70 base pairs of the alpha factor prepro (αfpp) coding sequence on one end and joins it to the 70 base pairs of the amino-terminus coding sequence from the mature zsig45 sequence on the other. The NEE-tagged linker (SEQ ID NO:21) joins Glu-Glu tag (SEQ ID NO:22) between the αFpp coding sequence and the zsig45 sequence. The untagged C-terminal linker (SEQ ID NO:23) spans about 70 base pairs of carboxy terminus coding sequence of the zsig45 on one end with 70 base pairs of AUG1 terminator sequence. The CEE-tagged linker (SEQ ID NO:24) inserts the Glu-Glu tag (SEQ ID NO:22) between the C-terminal end of zsig45 and the AUG1 terminator region. To make the NEE-tagged zsig45, the NEE-tagged linker and the untagged C-terminal linker were employed in the homologous recombination event; to make the CEE-tagged zsig45, the untagged N-terminal linker and the CEE-tagged linker were employed in the homologous recombination event.

Construction of the NEE-tagged-zsig45 Plasmid

An NEE-tagged-zsig45 plasmid was made by homologously recombining 100 ng of the SmaI digested pCZR204 acceptor vector, 1 μg of Eco RI-BamHI zsig45 cDNA donor fragment, 1 μg NEE-tagged-zsig45 linker (SEQ ID NO:21) and 1 μg of C-terminal untagged linker (SEQ ID NO:23) in *S. cerevisiae* (SF838–9D) (Rothman, J. et al., *EMBO J.* 8:2057–2065, 1989).

The NEE-zsig45 linker was synthesized by a PCR reaction. To a final reaction volume of 100 ml was added 1 pmol each of sense and antisense central oligos, ZC13,731 (SEQ ID NO:25) and ZC15,264 (SEQ ID NO:26) respectively; 100 pmol each of sense and antisense oligo primers, ZC13, 497 (SEQ ID NO:27) and ZC15,272 (SEQ ID NO:28) respectively; 10 μl of 10×PCR buffer (Boehringer Mannheim), 1 μl Pwo Polymerase (Boehringer Mannheim), 10 μl of 0.25 mM nucleotide triphosphate mix (Perkin Elmer) and dH$_2$O. The PCR reaction was run 10 cycles at 30 seconds at 94° C., 1 minute at 50° C. and 1 minute at 72° C., concluded with a 6 minute extension at 72°. The resulting 338 bp double stranded, NEE-tagged linker is disclosed in SEQ ID NO:21.

The C-terminal untagged zsig45 linker was made via a PCR reaction as described using sense and antisense central oligos, ZC15,725 (SEQ ID NO:29) and ZC15,633 (SEQ ID NO:30) respectively; and sense and antisense oligo primers, ZC15,271 (SEQ ID NO:31) and ZC13,734 (SEQ ID NO:32) respectively. The resulting 290 bp double stranded, C-terminal untagged linker is disclosed in SEQ ID NO:23.

Construction of the CEE-zsig45 Plasmid

A CEE-zsig45 plasmid was made by homologously recombining 100 ng of SmaI digested pCZR204 acceptor vector, the 1 μg of EcoRI-BamHI zsig45 cDNA donor fragment, 1 μg of N-terminal untagged zsig45 linker (SEQ ID NO:20) and 1 μg of CEE-tagged linker (SEQ ID NO:24) in a *S. cerevisiae*.

The N-terminal untagged zsig45 linker was made via a PCR reaction as described above using sense and antisense central oligos, ZC15,14,821 (SEQ ID NO:33) and ZC15,265 (SEQ ID NO:34) respectively; and sense and antisense oligo primers, ZC14,822 (SEQ ID NO:35) and ZC15,272 (SEQ ID NO:28) respectively. The resulting 244 bp double stranded, N-terminal untagged linker is disclosed in SEQ ID NO:20.

The CEE-tagged linker was made via a PCR reaction as described above using sense and antisense central oligos, ZC15,763 (SEQ ID NO:36) and ZC15,633 (SEQ ID NO:30) respectively; and sense and antisense oligo primers, ZC15, 271 (SEQ ID NO:31) and ZC13,734 (SEQ ID NO:32) respectively. The resulting approximately 288 bp double stranded, CEE-tagged linker is disclosed in SEQ ID NO:24.

One hundred microliters of competent yeast cells (*S. cerevisiae*) was independently combined with 10 ml of the various DNA mixtures from above and transferred to a 0.2 cm electroporation cuvette. The yeast/DNA mixtures were electropulsed at 0.75 kV (5 kV/cm), ∞ ohms, 25 μF. To each cuvette was added 600 μl of 1.2 M sorbitol and the yeast was plated in two 300 μl aliquots onto two URA D plates and incubated at 30° C.

After about 48 hours the Ura$^+$ yeast transformants from a single plate were resuspended in 2.5 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge as maximum speed. Three hundred microliters of the aqueous phase was transferred to a fresh tube and the DNA precipitated with 600 μl ethanol (EtOH), followed by centrifugation for 10 minutes at 4° C. The DNA pellet was resuspended in 100 μl H$_2$O.

Transformation of electrocompetent *E. coli* cells (MC1061; Casadaban, M. and S. Cohen, *J. Mol. Biol.* 138:179–207, 1980) was done with 1 μl yeast DNA prep and 50 μl of MC1061 cells. The cells were electropulsed at 2.0 kV, 25 μF and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was plated in 250 μl aliquots on four LB AMP plates (LB broth (Lennox), 1.8% Bacto™ Agar (Difco), 100 mg/L Ampicillin).

Individual clones harboring the correct expression construct for NEE and CEE tagged zsig45 constructs were identified by PCR and restriction digest, and sequence analysis was used to verify the presence of the zsig45 insert and to confirm that the various DNA sequences had been joined correctly to one another. Larger scale plasmid DNA was isolated using the Qiagen Maxi kit (Qiagen) according to manufacturer's instruction and the DNA was digested with NotI to liberate the Pichia-zsig45 expression cassette from the vector backbone. The NotI-restriction digested DNA fragment was then transformed into the *Pichia methanolica* expression host, PMAD16. This was done by mixing 100 μl of prepared competent PMAD16 cells with 10 μg of NotI restriction digested zsig45 and transferred to a 0.2 cm electroporation cuvette. The yeast/DNA mixture was electropulsed at 0.75 kV, 25 mF, infinite ohms. To the cuvette was added 1 ml of 1.2 M sorbitol and 500 μl aliquots were plated onto two ADE DS (0.056%-Ade-Trp-Thr powder, 0.67% yeast nitrogen base without amino acids, 2% D-glucose, 0.5% 200xtryptophan, threonine solution, and 18.22% D-sorbitol) plates for selection and incubated at 30° C. Clones were picked and screened via Western blot for high-level zsig45 expression. The resulting NEE-tagged-zsig45 plasmid containing yeast cells were designated PMAD16:pCZR207, and the CEE-tagged-zsig45 plasmid containing yeast cells were designated PMAD16:pCZR210. The clones were then subjected to fermentation.

Fermentation of *P. methanolica* PMAD16:pCZR207 for the expression of ZSIG45NEE was carried out in a 6.0 liter fed batch fermentation. The fermentation was started in 3.0 liters of basal medium plus glucose. The tank was inoculated from a 20 hour old shake flask grown in YEPD at 30° C. (8.0% v/v). Glucose dosing started at 12 hours into the run and ran at varied rates for the remainder of the fermentation. Induction of the AUG1 promoter driving expression of the ZSIG45NEE protein was turned on by the initiation of methanol dosing at 40 hours elapsed fermentation time (EFT). The fermentation ran for 72 hours and was harvested by centrifugation. From 5.5 liters of fermentation broth approximately 3.0 liters of cell broth was obtained after cell removal. A non-glycosylated protein was detected on western blots after probing with monoclonal antibody to the N terminal glu-glu tag.

Fermentation of *P. methanolica* PMAD16:pCZR210.1 for the expression of ZSIG45CEE was carried out as per above. A non-glycosylated protein was detected on western blots after probing with monoclonal antibody to the C terminal glu:glu tag.

Example 5

Purification of zsig45CEE and zsig45NEE Polypeptide from *Pichia methanolica* Infected Cells Unless otherwise noted, all operations were carried out at 4° C. The following procedure was used for purifying zsig45 polypeptide containing C-terminal or N-terminal GluGlu (EE) tags. A Protease inhibitor solution was added to 3000 ml of conditioned media from Pichia cultures (see, Example 4) to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). The sample was centrifuged at 10,000 rpm for 30 min. at 4° C. in a Beckman JLA-10.5 rotor (Beckman Instruments, Palo Alto, Calif.) in a Beckman Avanti J25I centrifuge (Beckman Instruments) to remove cell debris. To the supernatant fraction, 50.0 ml of anti-EE Sepharose (prepared as described below) was added, and the mixture was gently agitated on a Wheaton (Millville, N.J.) roller culture apparatus for 18.0 h at 4° C.

The mixture was poured into a 5.0×20.0 cm Econo-Column (Bio-Rad, Laboratories, Hercules, Calif.) and the anti-EE Sepharose gel was washed with 30 column volumes of phosphate buffered saline (PBS). The absorbance at 280 nM of the unretained flow-through fraction was measured until the absorbance was less than 0.05. The flow-through fraction was discarded. Once the absorbance of the flow-through was less than 0.05, column flow rate was reduced to zero. The anti-EE Sepharose gel was then washed with 2.0 column volumes of PBS containing 0.2 mg/ml EE peptide (Anaspec, San Jose, Calif.) for 1.0 h at 4° C. The EE peptide used has the sequence N-GluTyrMetProValAsp-C (SEQ ID NO:37). After washing, the column flow was resumed and the eluted polypeptide, containing both zsig45CEE (or zsig45NEE) polypeptide and EE peptide, was collected. This fraction is referred to as the "polypeptide elution fraction." The anti-EE Sepharose gel was washed with 2.0 column volumes of 0.1M glycine, pH 2.5, and the glycine wash was collected separately. The pH of the glycine-eluted fraction was adjusted to 7.0 by the addition of a small volume of 10×PBS and stored at 4° C. for future analysis if needed.

The polypeptide elution fraction was concentrated to 5.0 ml using a 3,000 molecular weight cutoff membrane concentrator (Millipore, Bedford, Mass.) according to the manufacturer's instructions. To separate zsig45CEE or zsig45NEE polypeptide from free EE peptide, the concentrated polypeptide elution fraction was subjected to chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions were collected and the absorbance at 280 nM was monitored. The first peak of material absorbing at 280 nM and eluting near the void volume of the column was collected. This material represented purified zsig45CEE or zsig45NEE polypeptide and was further characterized by SDS-PAGE and Western blotting with anti-EE antibodies.

On Coomassie Blue-stained SDS-PAGE gels, the zsig45 NEE preparation contained one major band of apparent molecular weight 8000. The mobility of this band was the same in the presence and absence of reducing agents and was visible on western blots with anti-EE antibodies. The zsig45 CEE purified protein also showed one major band at 8000 Da on Coomassie-Blue stained SDS-PAGE gels. Western blotting with anti-EE antibodies showed one major band of cross-reactive material at 8000 Da and a minor component at 18,000 Da. The mobility of the 8000 Da band on SDS-PAGE gels or western blots was not changed by the presence or absence of reducing agents.

The protein concentration of the purified proteins was performed by BCA analysis (Pierce, Rockford, Ill.) and the material was aliquoted, and stored at −80° C. according to our standard procedures. The concentrations of purified zsig45NEE polypeptide was 0.35 mg/ml and zsig45CEE polypeptide was 0.17 mg/ml.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

Example 6

Generation of Untagged zsig45 Recombinant Adenovirus

The protein coding region of zsig45 was amplified by PCR using primers that added FseI and AscI restriction sties at the 5' and 3' termini respectively. PCR primers ZC17536 (SEQ ID NO:38) and ZC17537 (SEQ ID NO:39) were used with template BluescriptSKII™ (Stratagene) plasmid containing the full-length zsig45 cDNA (Example 1) in a PCR reaction as follows: one cycle at 95° C. for 5 minutes; followed by 15 cycles at 95° C. for 1 min., 58° C. for 1 min., and 72° C. for 1.5 min.; followed by 72° C. for 7 min.; followed by a 4° C. soak. The PCR reaction product was loaded onto a 1.2% (low melt) SeaPlaque GTG (FMC, Rockland, Me.) gel in TAE buffer. The zsig45 PCR product was excised from the gel and purified using the QIAquick™ PCR Purification Kit gel cleanup kit as per kit instructions (Qiagen). The PCR product was then digested with FseI-AscI, phenol/chloroform extracted, EtOH precipitated, and rehydrated in 20 ml TE (Tris/EDTA pH 8). The 344 bp zsig45 fragment was then ligated into the FseI-AscI sites of the transgenic vector pTG12-8 (See, example 7) and transformed into DH10B competent cells by electroporation. Clones containing zsig45 were identified by plasmid DNA miniprep followed by digestion with FseI-AscI. A positive clone was sent to the sequencing department to insure there are no deletions or other anomalies in the construct. The sequence of zsig45 cDNA was confirmed. Qiagen Maxi Prep protocol (Qiagen) is used to generate DNA to continue our process described below.

Preparation of DNA Construct for Generation of Adenovirus

The 344 bp zsig45 cDNA was released from the TG12-8 vector using FseI and AscI enzymes. The cDNA was isolated on a 1% low melt SeaPlaque GTG™ (FMC, Rockland, Me.) gel and was then excised from the gel and the gel slice melted at 70° C., extracted twice with an equal volume of Tris buffered phenol, and EtOH precipitated. The DNA was resuspended in 10 μl H₂O.

The zsig45 cDNA was cloned into the FseI-AscI sites of pAdTrack CMV (He, T-C. et al., *PNAS* 95:2509–2514, 1998) in which the native polylinker was replaced with FseI, EcoRV, and AscI sites. Ligation was performed using the Fast-Link™ DNA ligation and screening kit (Epicentre Technologies, Madison, Wis.). In order to linearize the plasmid, approximately 5 μg of the pAdTrack CMV zsig45 plasmid was digested with PmeI. Approximately 1 μg of the linearized plasmid was cotransformed with 200 ng of supercoiled pAdEasy (He et al., supra.) into BJ5183 cells. The co-transformation was done using a Bio-Rad Gene Pulser at 2.5 kV, 200 ohms and 25 mFa. The entire co-transformation was plated on 4 LB plates containing 25 μg/ml kanamycin. The smallest colonies were picked and expanded in LB/kanamycin and recombinant adenovirus DNA identified by standard DNA miniprep procedures. Digestion of the recombinant adenovirus DNA with FseI-AscI confirmed the presence of zsig45. The recombinant adenovirus miniprep DNA was transformed into DH10B competent cells and DNA prepared using a Qiagen maxi prep kit as per kit instructions.

Transfection of 293a Cells with Recombinant DNA

Approximately 5 μg of recombinant adenoviral DNA was digested with PacI enzyme (New England Biolabs) for 3 hours at 37° C. in a reaction volume of 100 μl containing 20–30U of PacI. The digested DNA was extracted twice with an equal volume of phenol/chloroform and precipitated with ethanol. The DNA pellet was resuspended in 10 μl distilled water. A T25 flask of QBI-293A cells (Quantum Biotechnologies, Inc. Montreal, Qc. Canada), inoculated the day before and grown to 60–70% confluence, were transfected with the PacI digested DNA. The PacI-digested DNA was diluted up to a total volume of 50 μl with sterile HBS (150 mM NaCl, 20 mM HEPES). In a separate tube, 20 μl DOTAP (Boehringer Mannheim, 1 mg/ml) was diluted to a total volume of 100 μl with HBS. The DNA was added to the DOTAP, mixed gently by pipeting up and down, and left at room temperature for 15 minutes. The media was removed from the 293A cells and washed with 5 ml serum-free MEMalpha (Gibco BRL) containing 1 mM Sodium Pyruvate (GibcoBRL), 0.1 mM MEM non-essential amino acids (GibcoBRL) and 25 mM HEPES buffer (GibcoBRL). 5 ml of serum-free MEM was added to the 293A cells and held at 37° C. The DNA/lipid mixture was added drop-wise to the T25 flask of 293A cells, mixed gently and incubated at 37° C. for 4 hours. After 4 h the media containing the DNA/lipid mixture was aspirated off and replaced with 5 ml complete MEM containing 5% fetal bovine serum. The transfected cells were monitored for Green Fluorescent Protein (GFP) expression and formation of foci, i.e., viral plaques.

Seven days after transfection of 293A cells with the recombinant adenoviral DNA, the cells expressed the GFP protein and started to form foci. These foci are viral "plaques" and the crude viral lysate was collected by using a cell scraper to collect all of the 293A cells. The lysate was transferred to a 50 ml conical tube. To release most of the virus particles from the cells, three freeze/thaw cycles were done in a dry ice/ethanol bath and a 370 waterbath.

Amplification of Recombinant Adenovirus (rAdV)

The crude lysate was amplified (Primary (1°) amplification) to obtain a working "stock" of zsig45 rAdV lysate. Ten 10 cm plates of nearly confluent (80–90%) 293A cells were set up 20 hours previously, 200 ml of crude rAdV lysate added to each 10 cm plate and monitored for 48 to 72 hours looking for CPE under the white light microscope and expression of GFP under the fluorescent microscope. When all of the 293A cells showed CPE (Cytopathic Effect) this 1° stock lysate was collected and freeze/thaw cycles performed as described under Crude rAdV Lysate.

Secondary (2°) Amplification of zsig45 rAdV was obtained as follows: Twenty 15 cm tissue culture dishes of 293A cells were prepared so that the cells were 80–90% confluent. All but 20 mls of 5%MEM media was removed and each dish was inoculated with 300–500 ml 1° amplified rAdv lysate. After 48 hours the 293A cells were lysed from virus production and this lysate was collected into 250 ml polypropylene centrifuge bottles and the rAdV purified.

AdV/cDNA Purification

NP-40 detergent was added to a final concentration of 0.5% to the bottles of crude lysate in order to lyse all cells. Bottles were placed on a rotating platform for 10 min. agitating as fast as possible without the bottles falling over. The debris was pelleted by centrifugation at 20,000×G for 15 minutes. The supernatant was transferred to 250 ml polycarbonate centrifuge bottles and 0.5 volumes of 20%PEG8000/2.5M NaCl solution added. The bottles were shaken overnight on ice. The bottles were centrifuged at 20,000×G for 15 minutes and supernatant discarded into a bleach solution. The white precipitate in two vertical lines along the wall of the bottle on either side of the spin mark is the precipitated virus/PEG. Using a sterile cell scraper, the precipitate from 2 bottles was resuspended in 2.5 ml PBS. The virus solution was placed in 2 ml microcentrifuge tubes and centrifuged at 14,000×G in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of CsCl added. The CsCl was dissolved and 1 ml of this solution weighed 1.34 g. The solution was transferred polycarbonate thick-walled centrifuge tubes 3.2 ml (Beckman No. 362305) and spin at 80,000rpm (348,000×G) for 3–4 hours at 25° C. in a Beckman Optima TLX microultracentrifuge with the TLA-100.4 rotor. The virus formed a white band. Using wide-bore pipette tips, the virus band was collected.

The virus from the gradient has a large amount of CsCl which must be removed before it can be used on cells. Pharmacia PD-10 columns prepacked with Sephadex G-25M (Pharmacia) were used to desalt the virus preparation. The column was equilibrated with 20 ml of PBS. The virus was loaded and allow it to run into the column. 5 ml of PBS was added to the column and fractions of 8–10 drops collected. The optical densities of 1:50 dilutions of each fraction was determined at 260 nm on a spectrophotometer. A clear absorbance peak was present between fractions 7–12. These fractions were pooled and the optical density (OD) of a 1:50 dilution determined. A formula is used to convert OD into virus concentration: (OD at 260 nm) (50) $(1.1 \times 10^{12})$=virions/ml. The OD of a 1:50 dilution of the zsig45 rAdV was 0.057, giving a virus concentration of $3.1 \times 10^{12}$ virions/ml.

To store the virus, glycerol was added to the purified virus to a final concentration of 15%, mixed gently but effectively, and stored in aliquots at −80° C.

Tissue Culture Infectious Dose at 50% CPE (TCID 50) Viral Titration Assay

A protocol developed by Quantum Biotechnologies, Inc. (Montreal, Qc. Canada) was followed to measure recombinant virus infectivity. Briefly, two 96-well tissue culture plates were seeded with $1 \times 10^4$ 293A cells per well in MEM containing 2% fetal bovine serum for each recombinant virus to be assayed. After 24 hours 10-fold dilutions of each virus from $1 \times 10^{-2}$ to $1 \times 10^{-14}$ were made in MEM containing 2% fetal bovine serum. 100 µl of each dilution was placed in each of 20 wells. After 5 days at 37° C., wells were read either positive or negative for Cytopathic Effect (CPE) and a value for "Plaque Forming Units/ml" (PFU) is calculated.

$TCID_{50}$ formulation used was as per Quantum Biotechnologies, Inc., above. The titer (T) is determined from a plate where virus used is diluted from $10_{-2}$ to $10_{-14}$, and read 5 days after the infection. At each dilution a ratio (R) of positive wells for CPE per the total number of wells is determined.

To Calculate titer of the undiluted virus sample: the factor, "F"=1+d(S−0.5); where "S" is the sum of the ratios (R); and "d" is Log10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T).

The zsig45 adenovirus had a titer of $1.1 \times 10^{10}$ pfu/ml.

Example 7

Zsig45 Transgenic Mice

Oligonucleotides were designed to generate a PCR fragment containing a consensus Kozak sequence and the exact zsig45 coding region. These oligonucleotides were designed with an FseI site at the 5' end and an AscI site at the 3' end to facilitate cloning into pMT12-8, our standard transgenic vector. PMT12-8 contains the mouse MT-1 promoter and a 5' rat insulin II intron upstream of the FseI site.

PCR reactions were carried out with 200 ng human zsig45 template and oligonucleotides ZC17,536 (SEQ ID NO:38) and ZC17,537 (SEQ ID NO:39). PCR reaction conditions were as follows: 95° C. for 5 minutes; 15 cycles of 95° C. for 60 seconds, 62° C. for 60 seconds, and 72° C. for 90 seconds; and 72° C. for 7 minutes. PCR products were separated by agarose gel electrophoresis and purified using a QiaQuick™ (Qiagen) gel extraction kit. The isolated, 344 bp, DNA fragment was digested with FseI and AscI (Boerhinger-Mannheim), ethanol precipitated and ligated into pMT12-8 that was previously digested with FseI and AscI. The pMT12-8 plasmid, designed for expression of a gene of interest in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and grown in LB media containing 100 µg/ml ampicillin. Miniprep DNA was prepared from the picked clones and screened for the zsig45 insert by restriction digestion with EcoRI, and subsequent agarose gel electrophoresis. Maxipreps of the correct pMT-zsig45 construct were performed. A SalI fragment containing with 5' and 3' flanking sequences, the MT-1 promoter, the rat insulin II intron, zsig45 cDNA and the human growth hormone poly A sequence was prepared and used for microinjection into fertilized murine oocytes.

Fifteen transgenic mice were identified among 54 pups. Liver biopsies were performed on all 15 transgenics and the liver zsig45 transgene mRNA was quantified by RT-PCR. The expression profile was as follows: 3 high expressers (approximately 2400–5100 mRNA molecules/liver cell); 3 medium expressers (approximately 1600–1900 mRNA molecules/liver cell); 4 low expressers (approximately 200–400 mRNA molecules/liver cell); and 5 having no detectable transgene expression.

Example 8 zsig45 Activity In Vivo

Potential activity of the zsig45 protein was tested in normal mice by daily subcutaneous injection of the purified protein preparation over a 14 day period. The experiment used 34 male mice of the C57BL6 strain (Harlan Sprague Dawley, Indianapolis, Ind.) which were 8 weeks of age at the beginning of the study. The mice were divided into 4 groups: 10 mice received injections containing 10 micrograms of purified zsig45NEE polypeptide (See, Example 5) contained in 0.1 ml of phosphate buffered saline (PBS) with 0.1% Bovine serum albumin (BSA) (ICN Pharmaceuticals); 10 mice received injections containing 10 micrograms of purified zsig45CEE polypeptide (See, Example 5) contained in 0. 1 ml of PBS with 0.1% BSA; 9 mice received injections of the vehicle only (PBS containing 0.1% BSA; and 5 mice received no injection. The mice were weighed on day 0, 7, and 14. The mice were bled on day 7 and 14 for complete blood cell counts and to assess the mouse clinical chemistry panels using a mouse chemistry screen from Everett Central Laboratory, Everett Wash. On day 14 the mice were sacrificed and tissues were collected into formalin for histological analysis (see below).

The blood chemistry panels were completely normal and showed no significant differences between the groups of mice. Weight gain was not significnatly different between groups. Likewise, blood counts were all within normal range with no significant differences between groups.

Microscopic Evaluation of Skin

Skin samples (as well as other tissues) were isolated and prepared for histologic examination from animals subcutaneously administered zsig45CEE, zsig45-NEE or vehicle, bovine serum albumen (BSA) control. The skin was harvested approximately 2 weeks after initiation of the experimental treatment. Samples were fixed in 10% buffered formalin, embedded in paraffin, sectioned at 3 microns, and stained with hematoxylin and eosin. The slides were examined and scored as to severity of inflammation (0=none, 1=mild, 2=moderate, 3=severe) by a board certified veterinary pathologist blinded to treatment. The mean severity scores of each treatment group were determined and analyzed with a GraphPad InStata software package (GraphPad Software, San Diego, Calif.). The difference between the mean severity score of the zsig45-NEE group was significantly different than the animals given vehicle alone ($p<0.05$) by the Kruskal-Wallis test. The mean severity score of the zsig45-CEE (mean=2.1) group was similar to the zsig45-NEE group (mean=2.3) but was not significantly different than the controls (mean=1.2).

The skin slides were then randomly assorted, read by a boarded pathologist blinded to treatment, and ranked according to severity of inflammation from lowest to highest. With the exception of one control mouse (which may have inadvertently been mislabeled at necropsy), the controls were all in the lowest half of the severity rankings. The inflammation primarily occurred in the subcutis at the injection site. Less commonly, inflammatory foci were observed in the overlying deep dermis and underlying musculature. The inflammatory cells at the site consisted of lymphocytes, plasma cells, and macrophages with a smaller number of neutrophils, suggestive of chronic-active inflammation. There was also a mild to moderate increase in fibrous connective tissue at the site of injection. The inflammation and fibrosis observed in the treatment groups was greater than that observed in the control animals, and the inflammation observed in conjunction with zsig45-NEE was slightly greater than that observed with zsig45-CEE. The main difference between the BSA and zsig45 treated groups was in the severity and extent of the inflammation and fibrosis, being generally none to mild in the control (BSA treated) groups and moderate to severe in the zsig45 treated groups.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of producing an antibody to a polypeptide comprising:

inoculating an animal with a polypeptide selected from the group consisting of:

(a) a polypeptide consisting of 9 to 67 amino acids, wherein the polypeptide is identical to a contiguous sequence of amino acids in SEQ ID NO:2 from amino acid number 47 (Lys) to amino acid number 114 (Asp);

(b) a polypeptide consisting of the amino acid sequence of SEQ ID NO:2 from amino acid number 47 (Lys) to amino acid number 114 (Asp);

(c) a polypeptide consisting of the amino acid sequence of SEQ ID NO:4 from amino acid number 1 (Met) to amino acid number 85 (Asp);

(d) a polypeptide consisting of the amino acid sequence of SEQ ID NO:3 from amino acid number 1 (Met) to amino acid number 89 (Asp);

(e) a polypeptide consisting of the amino acid sequence of SEQ ID NO:2 from amino acid number 50 to 56;

(f) a polypeptide consisting of the amino acid sequence of SEQ ID NO:2 from amino acid number 61 to 66;

(g) a polypeptide consisting of the amino acid sequence of SEQ ID NO:2 from amino acid number 71 to 76;

(h) a polypeptide consisting of the amino acid sequence of SEQ ID NO:2 from amino acid number 87 to 92;

(i) a polypeptide consisting of the amino acid sequence of SEQ ID NO:2 from amino acid number 95 to 100; and (j) a polypeptide consisting of a hydrophilic peptide predicted from a hydrophobicity plot of the polypeptide as shown in SEQ ID NO:2 using a Hopp/Woods hydrophilicity profile based on a sliding six-residue window, with buried G, S, and T residues and exposed H, Y, and W residues ignored; and wherein the polypeptide elicits an immune response in the animal to produce the antibody; and isolating the antibody from the animal.

2. An antibody produced by the method of claim 1, which binds to a polypeptide as shown in SEQ ID NO:2.

3. The antibody of claim 2, wherein the antibody is a monoclonal antibody.

4. An antibody which binds to a polypeptide comprising a sequence of amino acid residues comprising an amino acid sequence selected from the group consisting of:

(a) the amino acid sequence as shown in SEQ ID NO:2 from amino acid number 47 (Lys) to amino acid number 114 (Asp) of SEQ ID NO:2;

(b) the amino acid sequence as shown in SEQ ID NO:4 from amino acid number 1 (Met) to amino acid number 85 (Asp);

(c) the amino acid sequence as shown in SEQ ID NO:3 from amino acid number 1 (Met) to amino acid number 89 (Asp);

(d) the amino acid sequence as shown in SEQ ID NO:2 from amino acid residue number 1 (Met) to amino acid residue number 114 (Asp).

5. The antibody of claim 4, wherein the antibody is a monoclonal antibody.

6. An antibody which binds to a polypeptide according to claim 4, wherein the polypeptide consists of a sequence of amino acid residues comprising an amino acid sequence selected from the group consisting of:

(a) the amino acid sequence as shown in SEQ ID NO:2 from amino acid number 47 (Lys) to amino acid number 114 (Asp) of SEQ ID NO:2;

(b) the amino acid sequence as shown in SEQ ID NO:4 from amino acid number 1 (Met) to amino acid number 85 (Asp);

(c) the amino acid sequence as shown in SEQ ID NO:3 from amino acid number 1 (Met) to amino acid number 89 (Asp);

(d) the amino acid sequence as shown in SEQ ID NO:2 from amino acid residue number 1 (Met) to amino acid residue number 114 (Asp).

* * * * *

SEQUENCE LISTING

```
<160> NUMBER OF SEQ ID NOS: 39

<210> SEQ ID NO 1
<211> LENGTH: 564
<212> TYPE: DNA
<213> ORGANISM: Homo sapiens
<220> FEATURE:
<221> NAME/KEY: CDS
<222> LOCATION: (81)...(422)

<400> SEQUENCE: 1
cccatccagg cagcacggct ggctgagcag agacaagggc tgcccacact gggactggta      60
gaggaagccg gccctgacgg atg ggt ggt ctc gcc ctt cct ggg ttc atc ctg     113
                     Met Gly Gly Leu Ala Leu Pro Gly Phe Ile Leu
                      1               5                  10 ctg cag gtg ggc ctg agt cgc aga tca gga agc acc ggg aag atg cag      161
Leu Gln Val Gly Leu Ser Arg Arg Ser Gly Ser Thr Gly Lys Met Gln
         15                  20                  25
```

```
gcc tgc atg gtg ccg ggg ctg gcc ctc tgc ctc cta ctg ggg cct ctt      209
Ala Cys Met Val Pro Gly Leu Ala Leu Cys Leu Leu Leu Gly Pro Leu
         30                  35                  40 gca ggg gcc aag cct gtg cag gag gaa gga gac cct tac gcg gag ctg      257
Ala Gly Ala Lys Pro Val Gln Glu Glu Gly Asp Pro Tyr Ala Glu Leu
 45                  50                  55 ccg gcc atg ccc tac tgg cct ttc tcc acc tct gac ttc tgg aac tat      305
Pro Ala Met Pro Tyr Trp Pro Phe Ser Thr Ser Asp Phe Trp Asn Tyr
 60                  65                  70                  75 gtg cag cac ttc cag gcc ctg ggg gcc tac ccc cag atc gag gac atg      353
Val Gln His Phe Gln Ala Leu Gly Ala Tyr Pro Gln Ile Glu Asp Met
                 80                  85                  90 gcc cga acc ttc ttt gcc cac ttc ccc ctg ggg agc acg ctg ggc ttc      401
Ala Arg Thr Phe Phe Ala His Phe Pro Leu Gly Ser Thr Leu Gly Phe
             95                 100                 105 cac gtt ccc tat cag gag gac tgaatggtgt ccagcctggt gcccgcccac         452
His Val Pro Tyr Gln Glu Asp
                 110 cccgccaggc tgcactcggt cgggcctcca caggatggag tcccgcaaaa actggcccct    512 gcaggaatca ggcctggtct cacgctcaat aaactccgga ctgaagatgc cc            564

<210> SEQ ID NO 2
<211> LENGTH: 114
<212> TYPE: PRT
<213> ORGANISM: Homo sapiens

<400> SEQUENCE: 2

Met Gly Gly Leu Ala Leu Pro Gly Phe Ile Leu Leu Gln Val Gly Leu
 1               5                  10                  15

Ser Arg Arg Ser Gly Ser Thr Gly Lys Met Gln Ala Cys Met Val Pro
             20                  25                  30

Gly Leu Ala Leu Cys Leu Leu Leu Gly Pro Leu Ala Gly Ala Lys Pro
         35                  40                  45

Val Gln Glu Glu Gly Asp Pro Tyr Ala Glu Leu Pro Ala Met Pro Tyr
     50                  55                  60

Trp Pro Phe Ser Thr Ser Asp Phe Trp Asn Tyr Val Gln His Phe Gln
 65                  70                  75                  80

Ala Leu Gly Ala Tyr Pro Gln Ile Glu Asp Met Ala Arg Thr Phe Phe
                 85                  90                  95

Ala His Phe Pro Leu Gly Ser Thr Leu Gly Phe His Val Pro Tyr Gln
            100                 105                 110

Glu Asp

<210> SEQ ID NO 3
<211> LENGTH: 89
<212> TYPE: PRT
<213> ORGANISM: Homo sapiens

<400> SEQUENCE: 3

Met Gln Ala Cys Met Val Pro Gly Leu Ala Leu Cys Leu Leu Leu Gly
 1               5                  10                  15

Pro Leu Ala Gly Ala Lys Pro Val Gln Glu Glu Gly Asp Pro Tyr Ala
             20                  25                  30

Glu Leu Pro Ala Met Pro Tyr Trp Pro Phe Ser Thr Ser Asp Phe Trp
         35                  40                  45

Asn Tyr Val Gln His Phe Gln Ala Leu Gly Ala Tyr Pro Gln Ile Glu
     50                  55                  60
```

```
Asp Met Ala Arg Thr Phe Phe Ala His Phe Pro Leu Gly Ser Thr Leu
 65                  70                  75                  80

Gly Phe His Val Pro Tyr Gln Glu Asp
                 85
```

<210> SEQ ID NO 4
<211> LENGTH: 85
<212> TYPE: PRT
<213> ORGANISM: Homo sapiens

<400> SEQUENCE: 4

```
Met Val Pro Gly Leu Ala Leu Cys Leu Leu Leu Gly Pro Leu Ala Gly
  1               5                  10                  15

Ala Lys Pro Val Gln Glu Glu Gly Asp Pro Tyr Ala Glu Leu Pro Ala
                 20                  25                  30

Met Pro Tyr Trp Pro Phe Ser Thr Ser Asp Phe Trp Asn Tyr Val Gln
             35                  40                  45

His Phe Gln Ala Leu Gly Ala Tyr Pro Gln Ile Glu Asp Met Ala Arg
         50                  55                  60

Thr Phe Phe Ala His Phe Pro Leu Gly Ser Thr Leu Gly Phe His Val
 65                  70                  75                  80

Pro Tyr Gln Glu Asp
                 85
```

<210> SEQ ID NO 5
<211> LENGTH: 6
<212> TYPE: PRT
<213> ORGANISM: Artificial Sequence
<220> FEATURE:
<223> OTHER INFORMATION: Motif 1 from zsig45 polypeptide

<400> SEQUENCE: 5

```
Gln Glu Glu Gly Asp Pro
  1               5
```

<210> SEQ ID NO 6
<211> LENGTH: 6
<212> TYPE: PRT
<213> ORGANISM: Artificial Sequence
<220> FEATURE:
<223> OTHER INFORMATION: Motif 2 from zsig45 polypeptide

<400> SEQUENCE: 6

```
Ala Met Pro Tyr Trp Pro
  1               5
```

<210> SEQ ID NO 7
<211> LENGTH: 6
<212> TYPE: PRT
<213> ORGANISM: Artificial Sequence
<220> FEATURE:
<223> OTHER INFORMATION: Motif 3 from zsig45 polypeptide

<400> SEQUENCE: 7

```
Asp Phe Trp Asn Tyr Val
  1               5
```

<210> SEQ ID NO 8
<211> LENGTH: 6
<212> TYPE: PRT
<213> ORGANISM: Artificial Sequence
<220> FEATURE:
<223> OTHER INFORMATION: Motif 4 from zsig45 polypeptide

```
<400> SEQUENCE: 8

Gln Ile Glu Asp Met Ala
 1               5

<210> SEQ ID NO 9
<211> LENGTH: 6
<212> TYPE: PRT
<213> ORGANISM: Artificial Sequence
<220> FEATURE:
<223> OTHER INFORMATION: Motif 5 from zsig45 polypeptide

<400> SEQUENCE: 9

Phe Phe Ala His Phe Pro
 1               5

<210> SEQ ID NO 10
<211> LENGTH: 17
<212> TYPE: DNA
<213> ORGANISM: Artificial Sequence
<220> FEATURE:
<223> OTHER INFORMATION: Degenerate polynucleotide sequence of Motif 1
<220> FEATURE:
<221> NAME/KEY: variation
<222> LOCATION: (1)...(17)
<223> OTHER INFORMATION: N is any nucleotide

<400> SEQUENCE: 10
cargargarg gngaycc                                                  17

<210> SEQ ID NO 11
<211> LENGTH: 17
<212> TYPE: DNA
<213> ORGANISM: Artificial Sequence
<220> FEATURE:
<223> OTHER INFORMATION: Degenerate polynucleotide sequence of Motif 2
<220> FEATURE:
<221> NAME/KEY: variation
<222> LOCATION: (1)...(17)
<223> OTHER INFORMATION: N is any nucleotide

<400> SEQUENCE: 11
gcnatgccnt aytggcc                                                  17

<210> SEQ ID NO 12
<211> LENGTH: 17
<212> TYPE: DNA
<213> ORGANISM: Artificial Sequence
<220> FEATURE:
<223> OTHER INFORMATION: Degenerate polynucleotide sequence of Motif 3

<400> SEQUENCE: 12
gayttytgga aytaygt                                                  17

<210> SEQ ID NO 13
<211> LENGTH: 17
<212> TYPE: DNA
<213> ORGANISM: Artificial Sequence
<220> FEATURE:
<223> OTHER INFORMATION: Degenerate polynucleotide sequence of Motif 4

<400> SEQUENCE: 13
carathgarg ayatggc                                                  17

<210> SEQ ID NO 14
<211> LENGTH: 17
<212> TYPE: DNA
<213> ORGANISM: Artificial Sequence
```

```
<220> FEATURE:
<223> OTHER INFORMATION: Degenerate polynucleotide sequence of Motif 5
<220> FEATURE:
<221> NAME/KEY: variation
<222> LOCATION: (1)...(17)
<223> OTHER INFORMATION: N is any nucleotide

<400> SEQUENCE: 14
ttyttygcnc ayttycc                                                      17

<210> SEQ ID NO 15
<211> LENGTH: 342
<212> TYPE: DNA
<213> ORGANISM: Artificial Sequence
<220> FEATURE:
<223> OTHER INFORMATION: Degenerate polynucleotide sequence of zsig45
      polypeptide
<220> FEATURE:
<221> NAME/KEY: variation
<222> LOCATION: (1)...(342)
<223> OTHER INFORMATION: N is any nucleotide

<400> SEQUENCE: 15
atgggnggny tngcnytncc nggnttyath ytnytncarg tnggnytnws nmgnmgnwsn        60
ggnwsnacng gnaaratgca rgcntgyatg gtnccnggny tngcnytntg yytnytnytn        20
ggnccnytng cnggngcnaa rccngtncar gargarggng ayccntaygc ngarytnccn        80
gcnatgccnt aytggccntt ywsnacnwsn gayttytgga aytaygtnca rcayttycar       40
gcnytnggng cntayccnca rathgargay atggcnmgna cnttyttygc ncayttyccn      100
ytnggnwsna cnytnggntt ycaygtnccn taycargarg ay                         142

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer ZC694

<400> SEQUENCE: 16
taatacgact cactataggg                                                   20

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer ZC14030

<400> SEQUENCE: 17
cgcagatcag gaagcaccgg gaaga                                             25

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide primer ZC15414

<400> SEQUENCE: 18
ttccacgttc cctatcag                                                     18

<210> SEQ ID NO 19
<211> LENGTH: 18
<212> TYPE: DNA
```

<210> ORGANISM: Artificial Sequence
<220> FEATURE:
<223> OTHER INFORMATION: Oligonucleotide primer ZC15413

<400> SEQUENCE: 19
tgcaggggcc agttttg                                                        18

<210> SEQ ID NO 20
<211> LENGTH: 244
<212> TYPE: DNA
<213> ORGANISM: Artificial Sequence
<220> FEATURE:
<223> OTHER INFORMATION: Untagged N-terminal linker

<400> SEQUENCE: 20 acgtttatt gtttatcaat actactattg ctagcattgc tgctaaagaa gaaggtgtaa          60
gcttggacaa gagagaatgc caaataacaa atagttatga tgataacgat cgtaacgacg        20
atttcttctt ccacattcga acctgttctc tcttaagcct gtgcaggagg aaggagaccc        80
ttacgcggag ctgccggcca tgccctactg gcctttctcc acctctttcg gacacgtcct       140
cctt                                                                    144

<210> SEQ ID NO 21
<211> LENGTH: 338
<212> TYPE: DNA
<213> ORGANISM: Artificial Sequence
<220> FEATURE:
<223> OTHER INFORMATION: N-terminal NEE-tagged linker

<400> SEQUENCE: 21
agcattgctg ctaaagaaga aggtgtaagc ttggacaaga gagaagaaga atacatgcca        60
atggaaggtg gttcgtaacg acgatttctt cttccacatt cgaacctgtt ctctcttctt      120
cttatgtacg gttaccttcc accaaagcct gtgcaggagg aaggagaccc ttacgcggag      180
ctgccggcca tgccctactg gcctttctcc acctttcgga cacgtcctcc ttcctctggg      240
aatgcgcctc gacggccggt acgggatgac cggaaagagg tggacctctg ggaatgcgcc      300
tcgacggccg gtacgggatg accggaaaga ggtggaga                              338

<210> SEQ ID NO 22
<211> LENGTH: 5
<212> TYPE: PRT
<213> ORGANISM: Artificial Sequence
<220> FEATURE:
<223> OTHER INFORMATION: Glu-glu tag sequence

<400> SEQUENCE: 22

Glu Tyr Pro Met Glu
 1               5

<210> SEQ ID NO 23
<211> LENGTH: 290
<212> TYPE: DNA
<213> ORGANISM: Artificial Sequence
<220> FEATURE:
<223> OTHER INFORMATION: Untagged C-terminal linker

<400> SEQUENCE: 23
ggcccgaacc ttctttgccc acttcccct ggggagcacg ctgggcttcc acgttcccta        60
tcaggaggac ccgggcttgg aagaaacggg tgaaggggga cccctcgtgc gacccgaagg      120
tgcaagggat agtcctcctg tagaattcgg ctgcctgttt ggatattttt ataattttg       180

```
agagtttgcc aactaatgtt tttctcttct atgatatctt aagccgacgg acaaacctat      240
aaaaatatta aaaactctca aacggttgat tacaaaaaga gaagatacta                 290
```

<210> SEQ ID NO 24
<211> LENGTH: 288
<212> TYPE: DNA
<213> ORGANISM: Artificial Sequence
<220> FEATURE:
<223> OTHER INFORMATION: C-terminal CEE-tagged linker

<400> SEQUENCE: 24

```
atggcccgaa ccttctttgc ccacttcccc tggggagca cgctgggctt ccacgttccc        60
tatcaggagg actaccgggc ttggaagaaa cgggtgaagg gggacccctc gtgcgacccg      120
aaggtgcaag ggatagtcct cctgggaggc gaggagtata tgcctatgga gtagaattcc     180
tagtattcta gggctgcctg tttggatatt tttatacctc cgctcctcat atacggatac     240
ctcatcttaa ggatcataag atcccgacgg acaaacctat aaaaatat                  288
```

<210> SEQ ID NO 25
<211> LENGTH: 51
<212> TYPE: DNA
<213> ORGANISM: Artificial Sequence
<220> FEATURE:
<223> OTHER INFORMATION: Oligonucleotide primer ZC13731

<400> SEQUENCE: 25

```
ggtgtaagct tggacaagag agaagaagaa tacatgccaa tggaaggtgg t                51
```

<210> SEQ ID NO 26
<211> LENGTH: 65
<212> TYPE: DNA
<213> ORGANISM: Artificial Sequence
<220> FEATURE:
<223> OTHER INFORMATION: Oligonucleotide primer ZC15264

<400> SEQUENCE: 26

```
ggcagctccg cgtaagggtc tccttcctcc tgcacaggct taccaccttc cattggcatg       60
tattc                                                                  65
```

<210> SEQ ID NO 27
<211> LENGTH: 44
<212> TYPE: DNA
<213> ORGANISM: Artificial Sequence
<220> FEATURE:
<223> OTHER INFORMATION: Oligonucleotide primer ZC13497

<400> SEQUENCE: 27

```
agcattgctg ctaaagaaga aggtgtaagc ttggacaaga gaga                       44
```

<210> SEQ ID NO 28
<211> LENGTH: 49
<212> TYPE: DNA
<213> ORGANISM: Artificial Sequence
<220> FEATURE:
<223> OTHER INFORMATION: Oligonucleotide primer ZC15272

<400> SEQUENCE: 28

```
aggtggagaa aggccagtag ggcatggccg gcagctccgc gtaagggtc                  49
```

<210> SEQ ID NO 29
<211> LENGTH: 65
<212> TYPE: DNA
<213> ORGANISM: Artificial Sequence
<220> FEATURE:
<223> OTHER INFORMATION: Oligonucleotide primer ZC15725

<400> SEQUENCE: 29
ctggggagca cgctgggctt ccacgttccc tatcaggagg actagaattc ggctgcctgt        60
ttgga                                                                   65

<210> SEQ ID NO 30
<211> LENGTH: 51
<212> TYPE: DNA
<213> ORGANISM: Artificial Sequence
<220> FEATURE:
<223> OTHER INFORMATION: Oligonucleotide primer ZC15633

<400> SEQUENCE: 30
tggcaaactc tcaaaaatta taaaaatatc caaacaggca gccgaattct a                 51

<210> SEQ ID NO 31
<211> LENGTH: 48
<212> TYPE: DNA
<213> ORGANISM: Artificial Sequence
<220> FEATURE:
<223> OTHER INFORMATION: Oligonucleotide primer ZC15271

<400> SEQUENCE: 31
ggcccgaacc ttctttgccc acttcccct ggggagcacg ctgggctt                      48

<210> SEQ ID NO 32
<211> LENGTH: 52
<212> TYPE: DNA
<213> ORGANISM: Artificial Sequence
<220> FEATURE:
<223> OTHER INFORMATION: Oligonucleotide primer ZC13734

<400> SEQUENCE: 32
atcatagaag agaaaaacat tagttggcaa actctcaaaa attataaaaa ta                52

<210> SEQ ID NO 33
<211> LENGTH: 62
<212> TYPE: DNA
<213> ORGANISM: Artificial Sequence
<220> FEATURE:
<223> OTHER INFORMATION: Oligonucleotide primer ZC14821

<400> SEQUENCE: 33
tcaatactac tattgctagc attgctgcta agaagaagg tgtaagcttg gacaagagag         60
aa                                                                      62

<210> SEQ ID NO 34
<211> LENGTH: 66
<212> TYPE: DNA
<213> ORGANISM: Artificial Sequence
<220> FEATURE:
<223> OTHER INFORMATION: Oligonucleotide primer ZC15265

<400> SEQUENCE: 34
ggcagctccg cgtaagggtc tccttcctcc tgcacaggct tttctctctt gtccaagctt        60
acacct                                                                  66

<210> SEQ ID NO 35
<211> LENGTH: 40
<212> TYPE: DNA
<213> ORGANISM: Artificial Sequence
<220> FEATURE:

```
<223> OTHER INFORMATION: Oligonucleotide primer ZC14822

<400> SEQUENCE: 35
acggtttatt gtttatcaat actactattg ctagcattgc                      40

<210> SEQ ID NO 36
<211> LENGTH: 18
<212> TYPE: DNA
<213> ORGANISM: Artificial Sequence
<220> FEATURE:
<223> OTHER INFORMATION: Oligonucleotide primer ZC15763

<400> SEQUENCE: 36
tccagctgcc catctaat                                              18

<210> SEQ ID NO 37
<211> LENGTH: 6
<212> TYPE: PRT
<213> ORGANISM: Artificial Sequence
<220> FEATURE:
<223> OTHER INFORMATION: EE Peptide

<400> SEQUENCE: 37

Glu Tyr Met Pro Val Asp
 1               5

<210> SEQ ID NO 38
<211> LENGTH: 32
<212> TYPE: DNA
<213> ORGANISM: Artificial Sequence
<220> FEATURE:
<223> OTHER INFORMATION: Oligonucleotide primer ZC17536

<400> SEQUENCE: 38
gtatacggcc ggccaccatg ggtggtctcg cc                              32

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer ZC17537

<400> SEQUENCE: 39
cgtacgggcg cgcctcagtc ctcctgatag gg                              32
```